(12) United States Patent
Marett

(10) Patent No.: US 7,438,691 B2
(45) Date of Patent: *Oct. 21, 2008

(54) METHOD AND DEVICE FOR PREDICTING THE FERTILE PHASE OF WOMEN

(75) Inventor: Douglas M. Marett, Toronto (CA)

(73) Assignee: HealthWatchSystems, Inc., Sarasota, FL (US)

( * ) Notice: Subject to any disclaimer, the term of this patent is extended or adjusted under 35 U.S.C. 154(b) by 57 days.

This patent is subject to a terminal disclaimer.

(21) Appl. No.: 10/485,784
(22) PCT Filed: Jul. 29, 2002
(86) PCT No.: PCT/CA02/01176

§ 371 (c)(1),
(2), (4) Date: Oct. 12, 2004

(87) PCT Pub. No.: WO03/011142

PCT Pub. Date: Feb. 13, 2003

(65) Prior Publication Data

US 2005/0042742 A1    Feb. 24, 2005

Related U.S. Application Data

(63) Continuation of application No. 09/917,739, filed on Jul. 31, 2001, now Pat. No. 6,592,529.

(51) Int. Cl.
*A61B 10/00* (2006.01)
*A61B 5/05* (2006.01)
(52) U.S. Cl. ........................ 600/551; 600/346
(58) Field of Classification Search ........ 600/551, 600/573, 584; 204/406, 407, 413, 415, 422
See application file for complete search history.

(56) References Cited

U.S. PATENT DOCUMENTS 4,454,007 A * 6/1984 Pace .............................. 205/778

(Continued)

FOREIGN PATENT DOCUMENTS

| EP | 0 090 327 | 3/1989 |
| WO | WO 94 03105 | 2/1994 |

OTHER PUBLICATIONS

Lieberman, "Cyclic Fluctuation of Sweat Electrolytes in Women", JAMA Feb. 21, 1996, vol. 195, No. 8, pp. 117-123.

(Continued)

*Primary Examiner*—Max Hindenburg
*Assistant Examiner*—Jonathan M Foreman
(74) *Attorney, Agent, or Firm*—Blakely, Sokoloff, Taylor & Zafman LLP

(57) ABSTRACT

A method and device to predict ovulation in a female human by measuring changes in the concentration of a number of ions in eccrine sweat is disclosed. The concentration, or changes in concentration, of one or more ions are determined throughout the day and analyzed against predetermined patterns in order to predict ovulation one to five days in advance. This permits the user to more accurately determine commencement of the fertile phase, which for female humans is generally considered to be about four days prior to ovulation to one day after ovulation. The concentration of the ions measured include sodium (Na+), potassium (K+), ammonium ($NH_4+$), calcium ($Ca_2+$), chloride (Cl−) and nitrate ($NO_3-$). To further increase the accuracy of the reading, a large number of readings can be obtained throughout a day and statistically analyzed to determine the change over time. In addition, the concentration of two or more ions can be obtained to increase accuracy. Ratiometric measurements between two or more ions can be determined to increase accuracy and account for ion accumulation on the skin. Ratiometric measurements between ammonium ($NH_4+$) and calcium ($Ca_2+$) have been found to provide more distinct patterns because the concentration of these two ions change in opposite directions during the relevant period preceding ovulation.

28 Claims, 16 Drawing Sheets

U.S. PATENT DOCUMENTS

| | | | |
|---|---|---|---|
| 4,653,499 | A | 3/1987 | Murray, Jr. |
| 4,770,186 | A | 9/1988 | Regas et al. |
| 4,814,060 | A | 3/1989 | Banks |
| 5,209,238 | A | 5/1993 | Sundhar |
| 5,467,778 | A * | 11/1995 | Catt et al. .................. 600/551 |
| 5,685,319 | A * | 11/1997 | Marett ........................ 600/551 |
| 6,198,953 | B1 * | 3/2001 | Webster et al. .............. 600/345 |
| 6,451,619 | B1 | 9/2002 | Catt et al. |
| 6,454,726 | B1 | 9/2002 | Catt et al. |
| 6,592,529 | B2 * | 7/2003 | Marett ........................ 600/551 |

OTHER PUBLICATIONS

Taylor et al., "Variation in Sweat Gland Function During the Menstrual Cycle", Journal of Investigative Dermatology, 1969, vol. 53, No. 3, pp. 234-237.

Eisenbeiss et al., "The Influence of Female Sex Hormones on Skin Thickness: Evaluation Using 20 MHz Sonography", British Journal of Dermatology 1998: 139: 462-467.

Jacobs et al., "Ovulation Prediction by Monitoring Salivary and Vaginal Electrical Resistance With the Peak Ovulation Predictor", May 1989, vol. 73, No. 5, Part I, pp. 817-822.

Fehring et al., "Accuracy of the Ovulation Fertility Monitor to Predict and Detect Ovulation", Journal of Nurse-Midwifery, Mar./Apr. 1988, vol. 43, No. 2, pp. 117-120.

Hartmann et al., "Acute Changes in the Composition of Milk During the Ovulatory Menstrual Cycle in Lactating Women", 1982, 324, pp. 21-30.

* cited by examiner

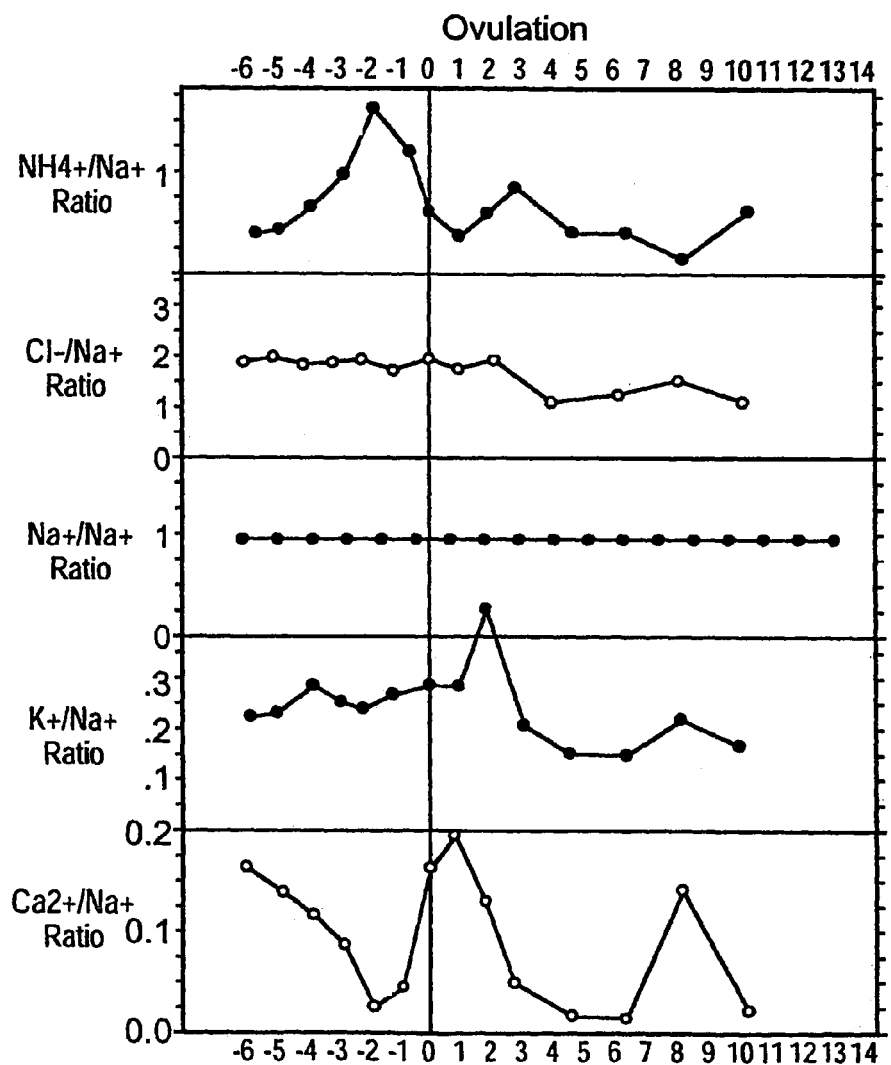

METHOD AND DEVICE FOR PREDICTING THE FERTILE PHASE OF WOMEN

CROSS-REFERENCE TO OTHER APPLICATIONS

This Application is a National Phase of International Application No. PCT/CA02/01176 filed on Jul. 29, 2002, which is a continuation application of U.S. patent application Ser. No. 09/917,739, filed on Jul. 31, 2001 now U.S. Pat. No. 6,592,529.

FIELD OF THE INVENTION

The present invention relates to a method and apparatus for determining fertility status of a female. More specifically, the invention relates to a method and apparatus for predicting ovulation and thereby determining the fertile phase from the non-fertile phase in the reproductive cycle of a female mammal, and preferably a female human.

BACKGROUND OF THE INVENTION

The fertile phase in a mammal can be defined as the period during which sperm present in the uterus may encounter and fertilize an egg. Generally, in female humans, the average reproductive cycle is 28 days, of which a released egg survives only about 12 to 24 hours. However, the uterus is capable of storing sperm for a period of up to four days. Thus, the fertile phase can commence up to four days prior to ovulation and last for up to one day after ovulation. But, the time period following ovulation, when an egg is released, is relatively narrow.

Many prior art devices have been proposed to determine when ovulation has occurred. However, by merely determining when ovulation has occurred, these prior art devices and methods only determine a fraction of the fertile phase in a female human. Clearly, an advantage can be obtained by predicting ovulation at least four days in advance, which will encompass the entire fertile phase of a woman. In this way, pregnancy can be planned.

Several methods for determining ovulation have been proposed in the past. In female humans, the maturation of ovarian follicles which will eventually release a fertile egg are effected by the action of Follicle Stimulating Hormone (FSH) and Luteinizing Hormone (LH) secreted by the anterior lobe of the pituitary. The ovulatory phase of the menstrual cycle is preceded by a significant rise in serum total estrogens 24 to 48 hours prior to ovulation, which prepare the uterus for possible implantation. The rise in estrogens is followed by a rapid rise in serum luteinizing hormone (LH) reaching a peak 12 to 24 hours prior to ovulation. Many other physiological conditions also change around the time of ovulation. For instance, basal body temperature (BBT) reaches a nadir followed by a sharp rise around the time of ovulation. Cervical mucus undergoes viscosity changes stimulated by rising estrogen which can help direct sperm towards the egg.

Several fertility detectors have been developed which measure these various hormones or their indirect physiological effects. The BBT method, referred to above, generally requires female humans to take their vaginal temperature and chart the value every morning before rising. Besides the considerable diligence involved, the method is generally only accurate within one to two days of ovulation, and gives no prior notice. Cervical mucus measurements have been regarded as somewhat more helpful. Women can examine their cervical mucus for a thinning of the mucus just before ovulation, which allows it to be drawn intact between the fingers and is referred to as the spinbarkeit reaction. Another method involves examining the cervical mucus under a microscope and looking for a "ferning" reaction indicative of imminent ovulation. A further method measures vaginal mucus conductivity using impedance probes which allows a somewhat more quantitative estimation of the mucus changes as disclosed in U.S. Pat. No. 4,770,186 . U.S. Pat. No. 5,209,238 to Sundhar discloses an ovulation monitor which determines the presence of a viable egg by sensing the mucous density, basil body temperature, and pH level and LH level of secretion in the vagina.

However, these prior art methods suffer from the disadvantage that they determine ovulation, but do not provide a means for predicting ovulation, thereby missing a large portion of the fertile phase. Also, cervical mucus examination suffers from subjective errors as well as being arduous and again gives little to no prior notice of ovulation.

U.S. Pat. No. 5,685,319 to Marett discloses that a significant pH nadir in female eccrine sweat was found to occur approximately five to six days prior to ovulation. In this way, tracking the pH of eccrine sweat could assist in predicting ovulation, and thereby determining the fertility status of a female human. Furthermore, an advantage of tracking pH is that it is inherently buffered in that the hydrogen ions $H^+$ can react with the hydroxide ion (OH) to form water. In addition, even though there is no satisfactory mechanism to explain skin acidity, previous studies have found that eccrine sweat of women is also generally buffered by either the lactic acid/lactate system, free amino acid secretion or $CO_2$ bicarbonate. The benefit of having the pH buffered is that changes in the quantity of eccrine sweat, such as through evaporation or increased physical activity, will not greatly affect the pH, thereby avoiding spurious readings.

Several researchers have also investigated changes of other ions in eccrine sweat. For instance, Lieberman and Taylor looked at chloride (Cl−), sodium (Na+) and potassium (K+) in the eccrine sweat of female humans (Lieberman et al. JAMA Feb. 21, 1996 , Vol. 195, No. 8, pages 117-123 and Taylor et al., Journal of Investigative Dermatology, Vol. 53, No. 3, pages 234-237, 1969). However, neither Lieberman nor Taylor investigated changes in the concentrations of these ions prior to ovulation and for the purpose of predicting ovulation.

One disadvantage of much of the prior art has been that it fails to predict ovulation at least three to six days in advance. Because of this, the prior art methods and devices fail to determine the entire fertile phase of a female.

Furthermore, other than for measuring pH, the prior art has failed to consider what other characteristics of eccrine sweat of female humans can be used to predict ovulation. The prior art has failed to provide a reliable and consistent method and device to obtain measurements of the characteristics of eccrine sweat, such as changes in the concentrations of ions, other than pH. In addition, the prior art has failed to provide a method and device which can measure changes in concentrations of ions in eccrine sweat which are not naturally buffered, as is pH, and which may therefore vary due to other factors, such as eccrine sweat volume due to increased physical activity, ambient temperature or evaporation.

Accordingly, there is a need in the art for a method and device to reliably and economically predict ovulation three to six days in advance in order to determine a larger portion of the fertile phase of a female mammal, and preferably a female human. There is also a need for a method and device to predict ovulation which is easy to use, reliable and inexpensive.

SUMMARY OF THE INVENTION

Accordingly, it is an object of this invention to at least partially overcome some of the disadvantages of the prior art. Also, it is an object of this invention to provide an improved method and device to assist in predicting ovulation in female mammals, and preferably female humans, about one to six days in advance, which is reliable and can be economically implemented.

Accordingly, in one of its aspects, this invention resides in a device for determining a fertile phase of a female human comprising: (a) a sensor for sensing concentrations of at least two ions in the eccrine sweat of the female and generating output signals indicative of concentrations of the at least two ions in the eccrine sweat; (b) a processor for controlling the sensor to sense the concentrations of at least two ions in the eccrine sweat substantially simultaneously and at least on a daily basis; and wherein the processor monitors the output signals from the sensor to identify a distinct change in the concentration of one of the at least two ions following an inversion which indicates the female human is in the fertile phase.

In a further aspect, the present invention resides in a device for determining the fertility status of a female mammal comprising: (a) a sensing means for sensing at least one ion selected from the group consisting of potassium ($K+$), ammonium ($NH_4+$), calcium ($Ca_2+$), chloride ($Cl-$), nitrate ($NO_3$) and sodium ($Na+$), in the eccrine sweat of the female mammal and generating output signals indicative of the concentration of ions in the eccrine sweat; (b) processor means for controlling the sensing means to sense the at least one ion in the eccrine sweat at least on a daily basis; and wherein the processor means monitors the output signals stored in the storage means to identify a distinct change in a concentration of one of the ions following an inversion which indicates the female mammal is in the fertile phase.

One advantage of the present invention is that changes in concentrations of several different types of ions in eccrine sweat can be sensed and analyzed to predict ovulation in female mammals. These ions include sodium ($Na+$), potassium ($K+$), ammonium ($NH_4+$), calcium ($Ca_2+$) and nitrate ($NO_3-$). In this way, different types of sensors can be selected to sense the corresponding ions, such as sodium ($Na+$), chloride ($Cl-$), ammonium ($NH_4+$), potassium ($K+$) calcium ($Ca_2+$) and nitrate ($NO_3-$). In addition, sensors to sense the conductivity of eccrine sweat, thereby indirectly measuring the total concentration of all of the ions, can be used. This permits a selection to be made as to which sensor is most reliable for a particular situation.

For instance, in colder climates where the user may excrete less eccrine sweat, a different type of ion, and a different type of sensor, could be used than in warmer climates where more eccrine sweat is excreted. Likewise, in veterinarian use, different sensors to sense different ions could be used depending on the particular situation and mammal whose fertility status is being sensed. Furthermore, this permits the sensor to be selected based on features other than reliability, such as cost and availability.

A further advantage of the present invention is that it provides for measurement of changes in concentrations of more than one ion in eccrine sweat. In this way, the changes in concentration of two or more ions can be monitored to provide confirmatory readings in order to more accurately predict ovulation and avoid false readings due to non-hormonal effects such as eccrine sweat volume, diet and stress.

A further advantage of measuring changes in concentration of more than one ion in eccrine sweat is that ratiometric measurements can be obtained. For example, it has been discovered that sodium ($Na+$) and chloride ($Cl-$) ions in eccrine sweat are the dominant ions and can be used to reference the rate of sweating. By using sodium ($Na+$) or chloride ($Cl-$) as a reference ion, the concentration changes in other ions in relation to sodium ($Na+$) and chloride ($Cl-$) can be assessed. The ratio of chloride ($Cl-$), to sodium ($Na+$) is particularly constant, which is expected because chloride ($Cl-$) is the main counter ion for sodium ($Na+$). While the concentrations of chloride ($Cl-$) and sodium ($Na+$) ions can each be measured individually to predict ovulation, these ions can also be used in order to account for changes in concentrations of the other ions, such as potassium ($K+$), ammonium ($NH_4+$), calcium ($Ca_2+$) and nitrate ($NO_3-$), due to changes in the quantity of eccrine sweat, such as through evaporation, increased ambient temperature, increased physical activity or ion accumulation on the skin over time. This is the case because while sodium ($Na+$) and chloride ($Cl-$) surge prior to ovulation, they do not surge as much as other ions, such as nitrate ($NO_3-$), calcium ($Ca_2+$) and ammonium ($NH_4+$). Accordingly, by performing a ratiometric measurement between one of the ions, such as potassium ($K+$), ammonium ($NH_4+$), calcium ($Ca_2+$) or nitrate ($NO_3-$), with respect to either sodium ($Na+$) and/or chloride ($Cl-$), a more consistent measurement of the ions can be obtained, and changes in concentration due to changes in eccrine sweat volume and ion accumulation on the skin over the day can be accounted for to some extent. In this way, a more accurate measurement can be made.

A still further advantage of the present invention is that some of the ions have been found to have counteracting effects. For instance, the concentration of calcium ($Ca_2+$) has been found to change in the opposite direction during the time period of interest preceding ovulation. In this way, performing a ratiometric measurement of calcium ($Ca_2+$) with respect to another ion, such as ammonium ($NH_4+$), can improve prediction because a more pronounced effect will be monitored.

In order to further improve the prediction, three ions may be measured, such as ammonium ($NH_4+$), calcium ($Ca_2+$) and either sodium ($Na+$) or chloride ($Cl-$). Measurements can then be made with respect to ammonium ($NH_4+$) and sodium ($Na+$), as well as sodium ($Na+$) and calcium ($Ca_2+$), to account for changes in concentrations of all of the ions due to accumulation on the skin or changes in eccrine sweat volume due to temperature and/or physical activity. These two ratiometric measurements can then be compared to obtain a ratiometric measurement of ammonium ($NH_4+$) with respect to calcium ($Ca_2+$), but with some of the changes due to other effects accounted for because the concentrations of ammonium ($NH_4+$) and calcium ($Ca_2+$) were initially measured with respect to sodium ($Na+$).

A further advantage of the present invention relates to one embodiment where the method is implemented by means of a device that is in contact with the skin for extended periods of time, such as 12 hours on a daily basis. This facilitates taking several readings over the course of a day so that a better statistical analysis can be performed. Furthermore, by taking several readings over the course of a day, spurious readings can be identified and eliminated. Furthermore, the device can, in a preferred embodiment, sense when it is not on the skin so that a reading will not be taken at this time. This obviously decreases the number of incorrect readings, while at the same time, not adversely affecting the overall daily reading, because a large number of other readings will likely be obtained during the course of the day and can be used to obtain a reliable average. In other words, by taking a large number of readings, such as 10 to 48, over a period of time, such as 24 hours, and statistically examining these readings, changes in eccrine sweat not related to menstrual hormones can be largely removed.

A still further advantage of the present invention is that readings from previous reproductive cycles can be stored for the same female. These stored readings can be used to better predict ovulation by ignoring readings taken during the early part of the reproductive cycle. For instance, if it is known from previous reproductive cycles that a particular female human never ovulates within four days of menstruation starting, the readings at the beginning of the reproductive cycle, following menstruation will be given less weight in predicting ovulation in the future. In a preferred embodiment, the duration of the reproductive cycle is determined and then, for female humans, ovulation is estimated to occur at some time in the last 19 days of the reproductive cycle. This coincides with the Luteal period which is generally 14 days from ovulation to menstruation for humans. Accordingly, the portion of the reproductive cycle prior to 19 days from the estimated start of menstruation is given less weight or disregarded for the purposes of determining the fertile phase of the female.

Further aspects of the invention will become apparent upon reading the following detailed description and drawings which illustrate the invention and the preferred embodiments of the invention.

BRIEF DESCRIPTION OF THE DRAWINGS

In the drawings, which illustrate embodiments of the invention:

FIGS. 3A to 3E are diagrams showing ratiometric measurements of ammonium ($NH_4+$), chloride ($Cl-$), sodium ($Na+$), potassium ($K+$) and calcium ($Ca_2+$) with respect to sodium ($Na+$) during one reproductive cycle of a female human;

DETAILED DESCRIPTION OF THE PREFERRED EMBODIMENTS

The present invention involves a method and device to predict ovulation in female mammals, such as the female human, several days in advance by monitoring changes in eccrine sweat. Ovulation is preferably predicted in advance by at least one half of the time period that sperm is capable of surviving within the female mammal so that a larger portion of the fertile phase can be determined. In this way, the present invention provides a reliable self-monitoring personal use test to permit determination of substantially the entire fertile phase of the female. It can also be used by a physician in the treatment of female infertility since many diagnostic or therapeutic measures depend on the accurate prediction and detection of ovulation.

Eccrine sweat is a thin watery fluid which is secreted onto the surface of skin by the eccrine sweat glands. Generally, thick skin, such as the palms, is abundantly supplied by eccrine sweat glands, but they are also found in substantial numbers in thin skin.

In humans, eccrine sweat secretions are complex systems containing several electrolytes or ions including sodium (30 to. 150 mmol), potassium (10 to 40 mmol) and chloride (40 to 110 mmol). It also contains non-electrolyte components, such as lactate, urea, glucose, protein, free amino acids, and lipids.

It has been found that the ions present in eccrine sweat, such as sodium ($Na+$), potassium ($K+$), nitrate ($NO_3-$), calcium ($Ca_2+$) and chloride ($Cl-$), appear to be released in a pattern linked with ovulation. Although variability does exist in the concentration of ions in eccrine sweat from female to female, the pattern of change in the concentration of ions in eccrine sweat has been found to repeat during the reproductive cycle to permit prediction of ovulation up to 70% to 90% accuracy.

Figure 1A:
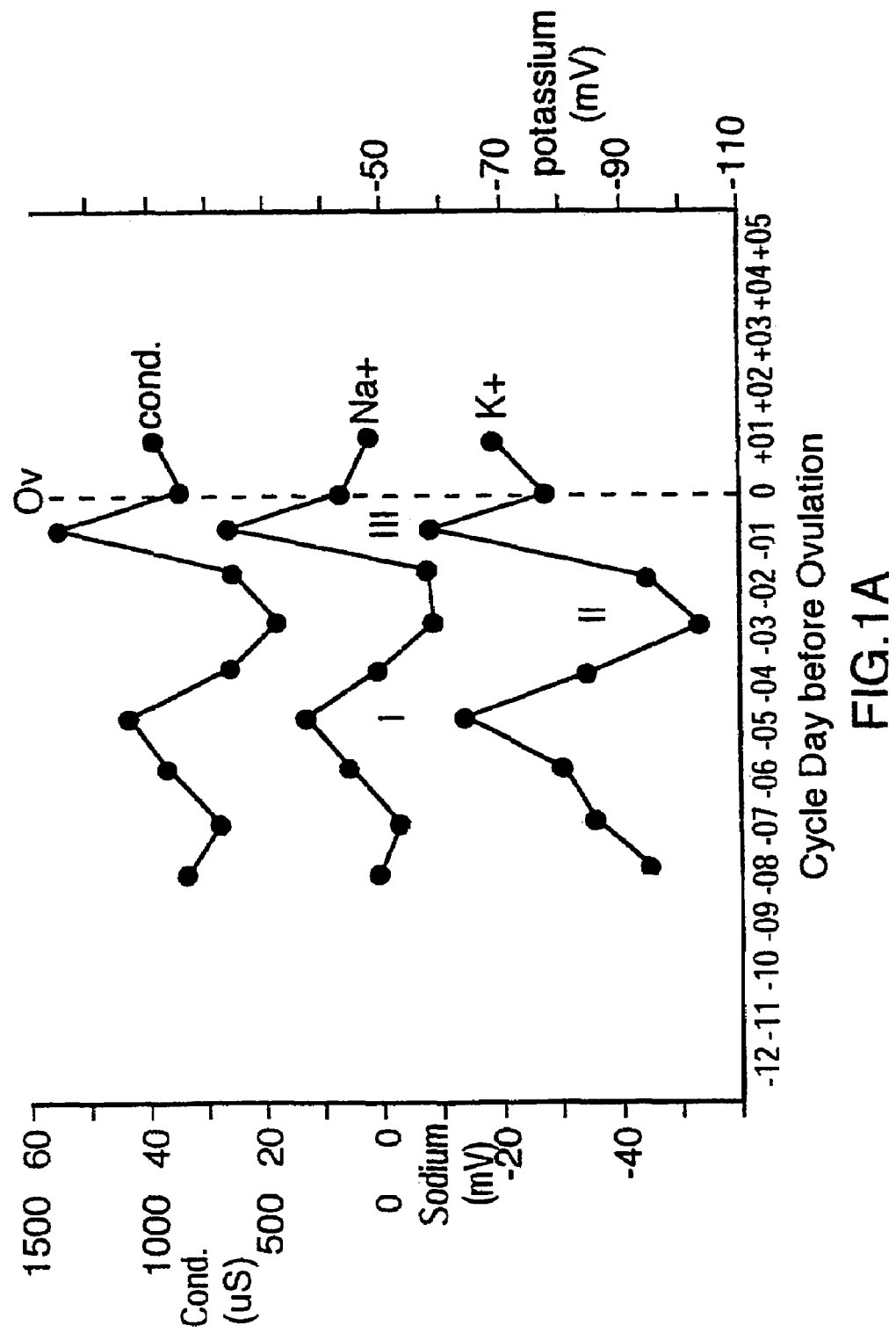
FIGS. 1A, 1B and 1C are diagrams illustrating changes in the concentrations of potassium ($K+$) and sodium ($Na+$) ions in eccrine sweat, as well as sweat conductivity during one reproductive cycle of a female human.
Figure 1B:
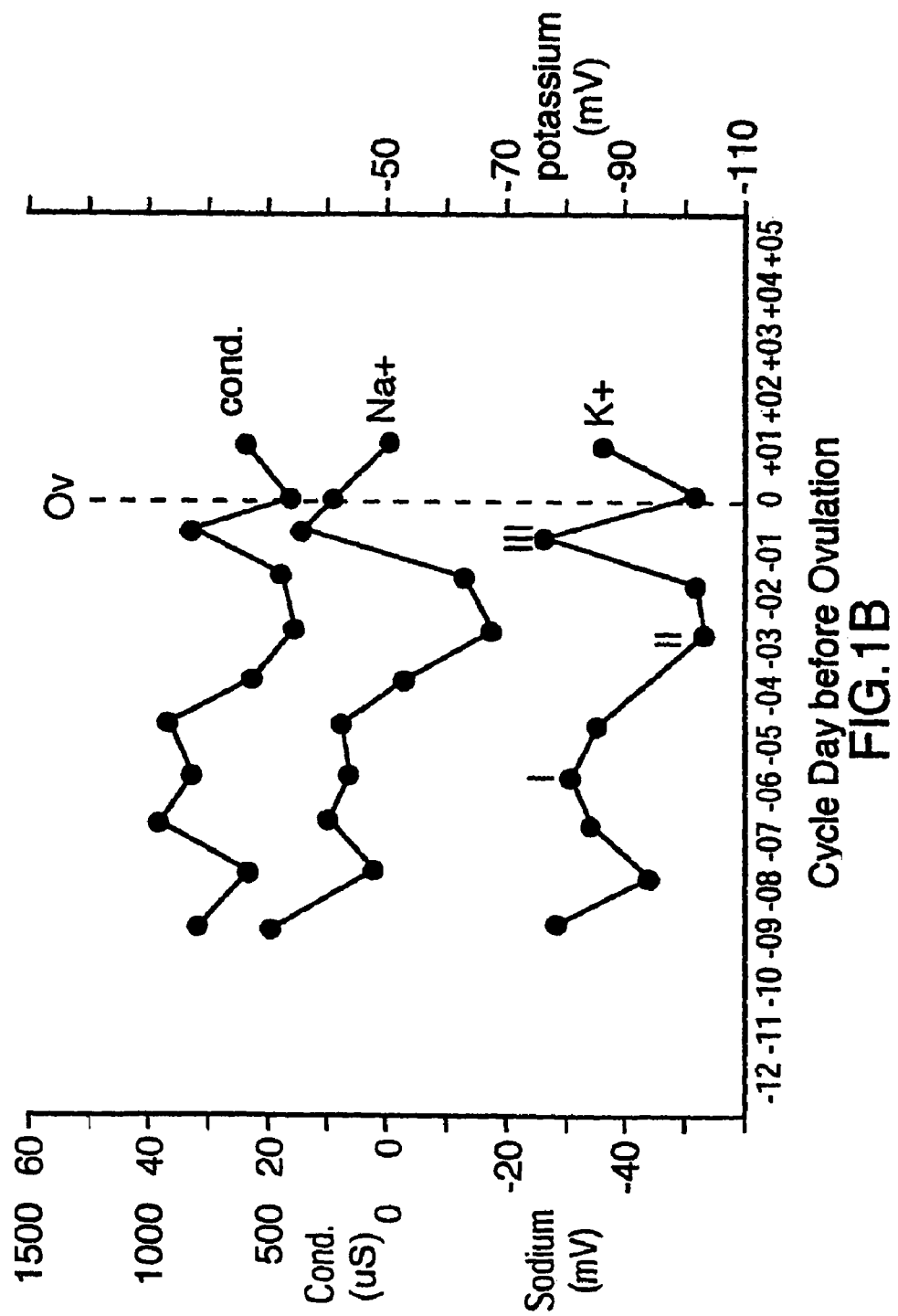
Figure 1C:
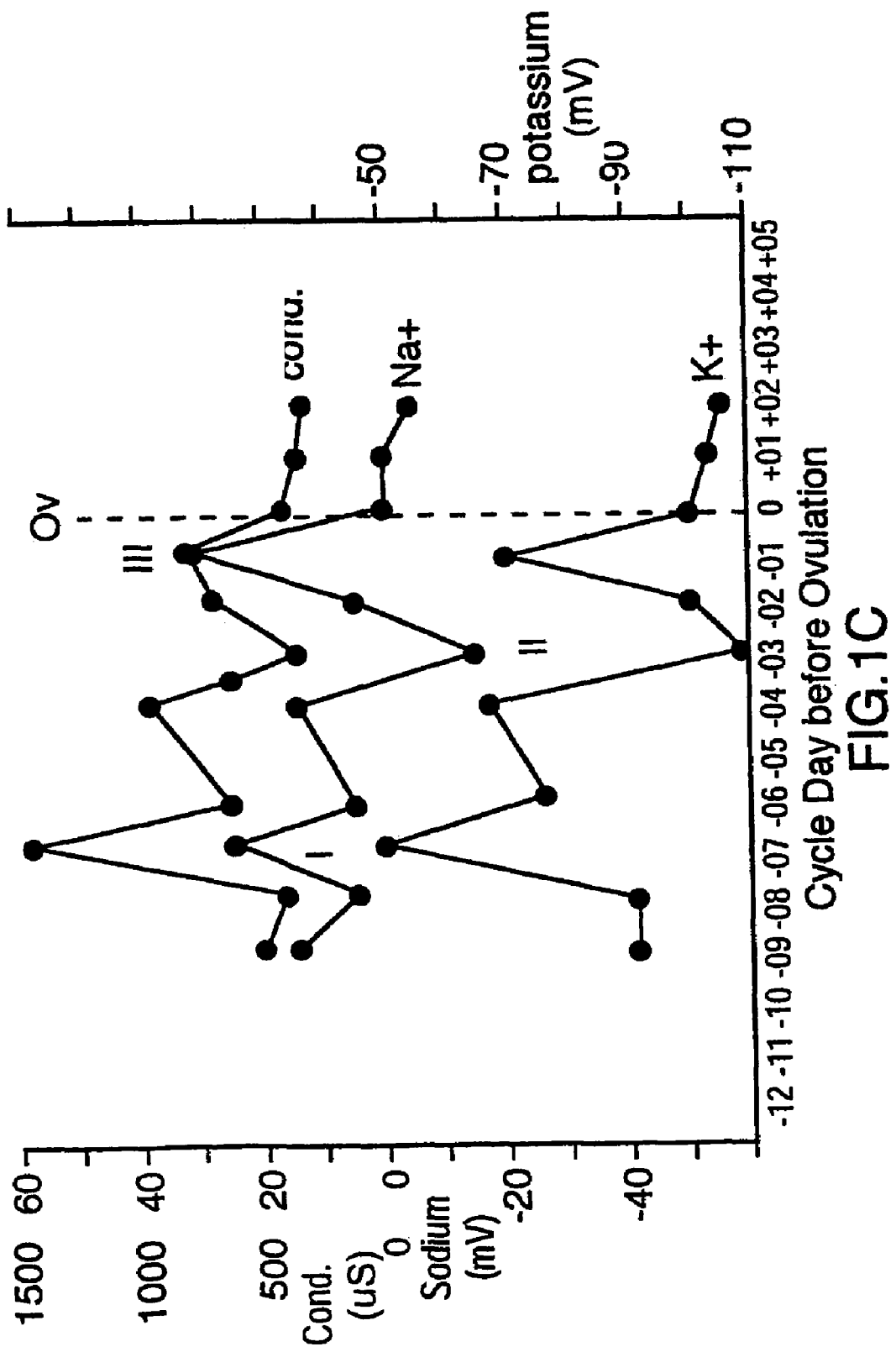
Figure 1D:
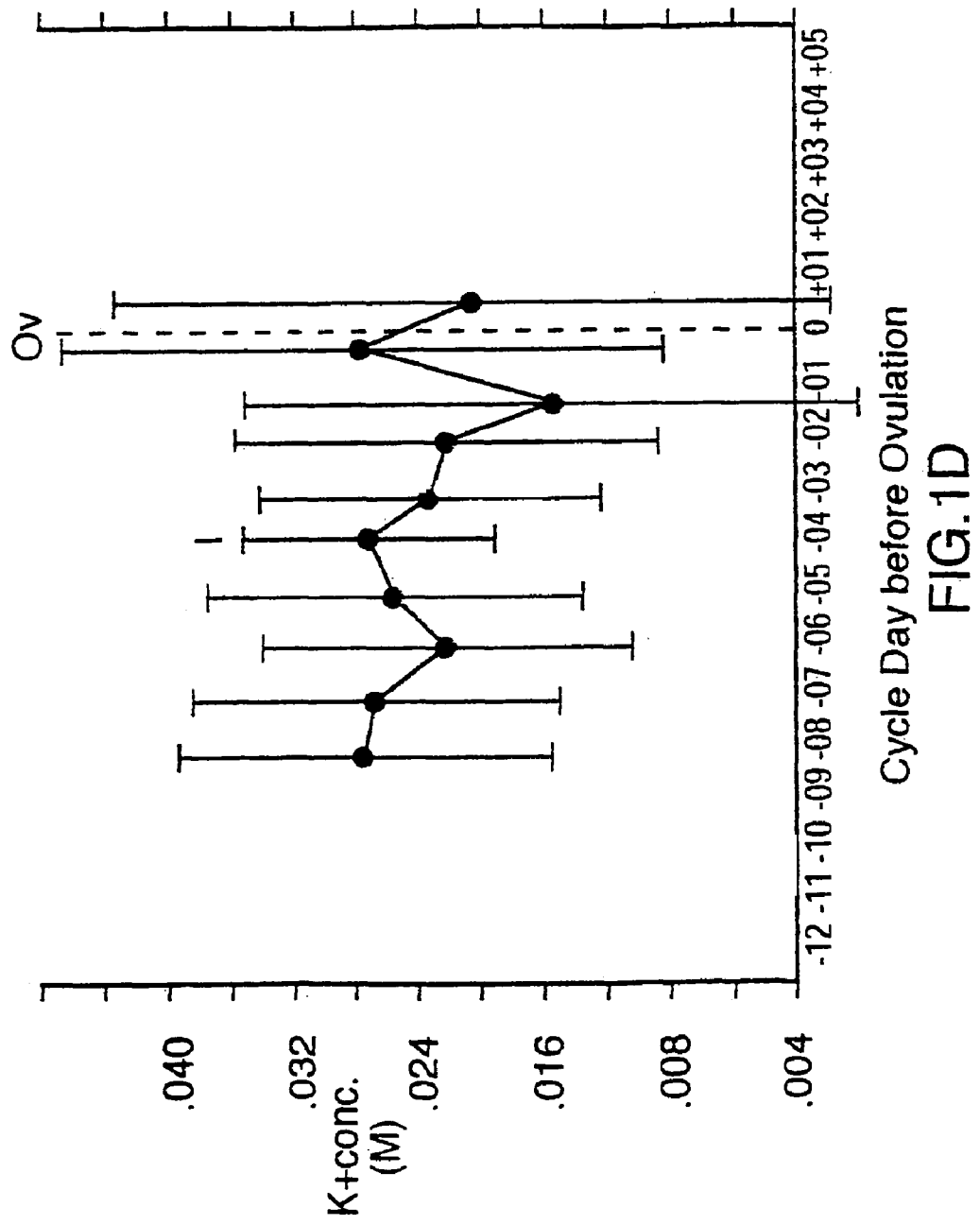
FIG. 1D is a diagram illustrating changes in the concentration of potassium ($K+$) ions in eccrine sweat.

FIGS. 1A to 1C illustrate measurements made of the concentrations of sodium ($Na+$) and potassium ($K+$) ions in eccrine sweat on a daily basis during the reproductive period of a female human. FIGS. 1A to 1C show the concentration of the sodium ($Na+$) and potassium ($K+$) ions in millivolts. FIG. 1D illustrates the concentration of potassium ($K+$) ions in the eccrine sweat of the female human measured on a daily basis in mols M.

FIGS. 1A to 1C also illustrate changes in the conductivity (Cond.) of the eccrine sweat, in microsiemens (uS). It is understood that the conductivity of eccrine sweat will change with the total number of ions present. Therefore, measuring conductivity is an indirect method of measuring the total number of ions in the eccrine sweat.

The adscissa in FIGS. 1A to 1C, as well as the other figures showing changes in concentration, shows the cycle days for one reproductive cycle of a female human. For convenience, day 0 on the adscissa corresponds with the day of ovulation, which is also indicated by the vertical dashed line "Ov". The day of ovulation "Ov" was determined by one of the conventional methods, namely detection of the Luteinizing Hormone (LH) which can determine ovulation within about 24 hours.

The values for FIGS. 1A to 1D are indicated by dots and represent daily averages of a number of readings taken over the day, such as 10 to 20 in number. This is done to increase accuracy and decrease the effects of non-hormonal changes in the concentrations of those ions.

FIG. 1D charts the potassium (K+) ion concentration of eccrine sweat of the female human measured in mols M on a daily basis, while FIGS. 1A to 1C chart the concentration for these ions in millivolts. This is the case merely because FIGS. 1A to 1C illustrate the value of the electrical signal from the sensor for the ion, which is in millivolts, while FIG. 1D illustrates the converted value of the concentration in mols M. However, it is understood that the value for the electrical potential signals in FIGS. 1A to 1C reflect the concentration of the sodium (Na+) and potassium (K+) ions, and could be converted to mols M, as was done in FIG. 1D. Furthermore, it is understood that the pattern to determine ovulation is based greatly on the changes in concentration, and therefore the absolute value of the concentration is not as important as changes in the concentration over time. The changes in concentration can be determined from both the electrical potential signals illustrated in FIGS. 1A, 1B and 1C and the molar values illustrated in FIG. 1D.

As illustrated in FIGS. 1A to 1D, there is a distinct change in the concentration of both sodium (Na+) and potassium (K+) ions in eccrine sweat at about five days prior to ovulation following an inversion at about seven days before ovulation. Likewise, there is a distinct change in the conductivity, as shown in FIGS. 1A, 1B and 1C at about five to seven days before ovulation following an inversion at about seven days before ovulation. This point of an inversion is indicated by Roman numeral I in each of FIGS. 1A to 1D.

The inversion indicated by reference numeral I in FIGS. 1A to 1D is generally identified by the distinct change, in this case a decrease, in the concentration, generally in the range of about 40% over the previous value of the previous day. For FIGS. 1A to 1C, which are in millivolts, this distinct change in concentration following the inversion is generally shown by a decrease of about 13 millivolts, corresponding to about a 40% decrease in the concentration from the previous day's value. Therefore, the distinct change is a decrease of 40% from the peak or highest value which occurs on or near the day of inversion.

As shown in FIGS. 1A and 1C, the inversion is also identified by an earlier surge of about five millivolts, which corresponds to about a 25% increase, in the concentration of the sodium (Na+) and potassium (K+) ions. This surge of about 25% in the sodium (Na+) and potassium (K+) ion concentration, followed by the 40% or 13 millivolt decrease, assists in delineating the inversion at point I, which indicates commencement of the fertile phase.

FIG. 1D, which illustrates the molar concentration of the potassium ion (K+) illustrates a similar increase of about 25%, followed by a decrease of 40%. Accordingly, it is apparent that the change in ion concentrations, whether measured in millivolts or converted to mols M or any other units, can be used to delineate the inversion at point I.

The method and device according to the present invention monitors the output signals from a sensor detecting the concentration of ions, in the case of FIGS. 1A to 1C potassium (K+) and sodium (Na+) to identify a surge of at least 25% in concentration, followed by a drop of about 40% in concentration. For FIGS. 1A and 1C, which chart changes in the potential of a sensor for these ions in millivolts, this corresponds to a five millivolt increase and a 13 millivolt decrease, occurring over a three to five day period based on daily averages. Identifying this pattern in the change of concentration of the ions indicates commencement of the fertile phase in the female human.

An analysis of FIGS. 1A, 1B and 1C also illustrates the benefit of measuring the change in concentration of more than one ion in eccrine sweat. In particular, as illustrated in FIG. 1B, while there is a clear inversion resulting from a maximum for the potassium (K+) ion concentration on the sixth day before ovulation, there is a less distinct inversion or maximum for the sodium (Na+) ion concentration. Rather, the sodium (Na+) ion concentration experiences an inversion or maximum followed by a distinct decrease of 40% on the fifth day before ovulation. Accordingly, by monitoring two ion concentrations, a more accurate prediction of ovulation may occur by identifying a distinct change in the concentration of one of the at least two ions following an inversion which indicates the female human is in the fertile phase.

As also illustrated in FIGS. 1A and 1B, following the inversion, which in this case is a maximum, as identified by Roman numeral I, the concentration reaches a maximum or peak at Roman numeral II, which is generally about one to two days prior to ovulation. This is followed by a further minimum or nadir shown at Roman numeral III, which generally occurs the day before or after ovulation. However, it is understood that because the fertile phase in a female mammal, such as a female human, can begin up to four days prior to ovulation, the nadir at Roman numeral I followed by about a 40% change can best be used to indicate commencement of the fertile phase.

With respect to the sodium (Na+) or potassium (K+) ions, an inversion resulting from a maximum or peak has been found to occur at commencement of the fertile phase, identified by Roman numeral I, as referred to above. However, it is understood that the maximum is a particular type of inversion in the direction of change of the ion concentration. For example, other ions, such as calcium ($Ca_2+$), have been found to reach a minimum rather than a maximum. Accordingly, it is understood that an inversion in the concentration can be a minimum (nadir) or maximum (peak), followed by a distinct change which is generally about a 40% change.

Accordingly, FIGS. 1A to 1D illustrate changes in the concentrations of ions, such as potassium (K+) and sodium (Na+), as well as changes in the total concentration of all of the ions, as shown by changes in conductivity (Cond.). As stated above, these changes in concentration of ions in eccrine sweat can be used to determine that a female mammal, such as a female human, is in the fertile phase. Furthermore, this determination can be made several days before ovulation actually occurs, in order to benefit from the entire fertile phase of the female human.

In particular, FIGS. 1A to 1D illustrate that a distinct change, which in this case is a decrease, in the concentration of one of at least two ions, such as potassium (K+) and/or sodium (Na+), following an inversion, which in this case is a peak at point I, indicates the female human is in the fertile phase. Moreover, measuring conductivity provides a general indication of the changes in the concentration of the total number of ions in eccrine sweat and has been found to also change in similar ways. Furthermore, at least for sodium (Na+) and potassium (K+), the inversion followed by a distinct change, can be identified by a surge of about 25%, or about five millivolts, as illustrated in FIGS. 1A to 1C, followed by a drop of about 40%, or about 13 millivolts. This surge followed by a drop defines an inversion, which in this case is a peak or maximum. Identification of this inversion, followed by the distinct change, in this case the drop of about 40%, indicates the female human is in the fertile phase. Other ions, such as chloride, ammonium ($NH_4+$), calcium ($Ca_2+$), and nitrate ($NO_3-$) have been discovered to behave in similar ways, as described more fully below.

Figure 2A:
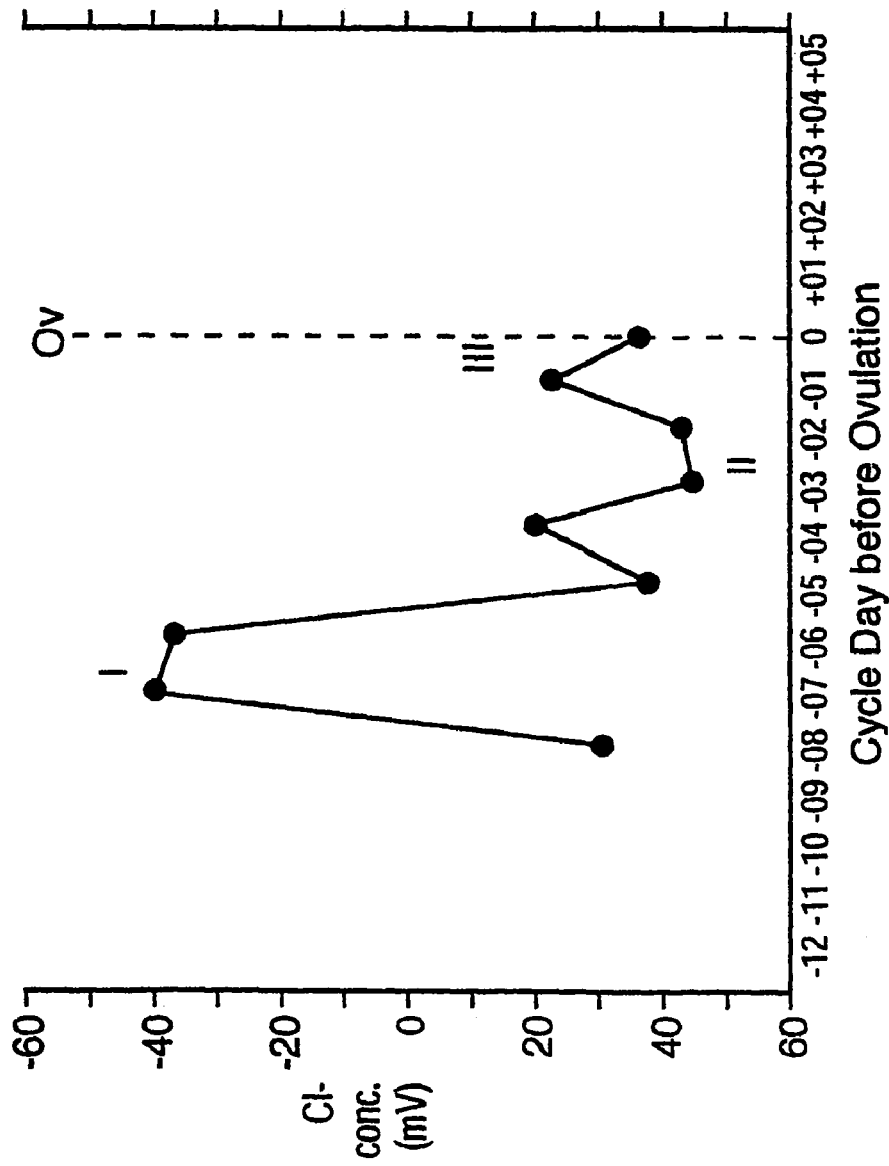
FIGS. 2A, 2B and 2C are diagrams illustrating the concentration of chloride ($Cl-$) ions in eccrine sweat, during one reproductive cycle of a female human.
Figure 2B:
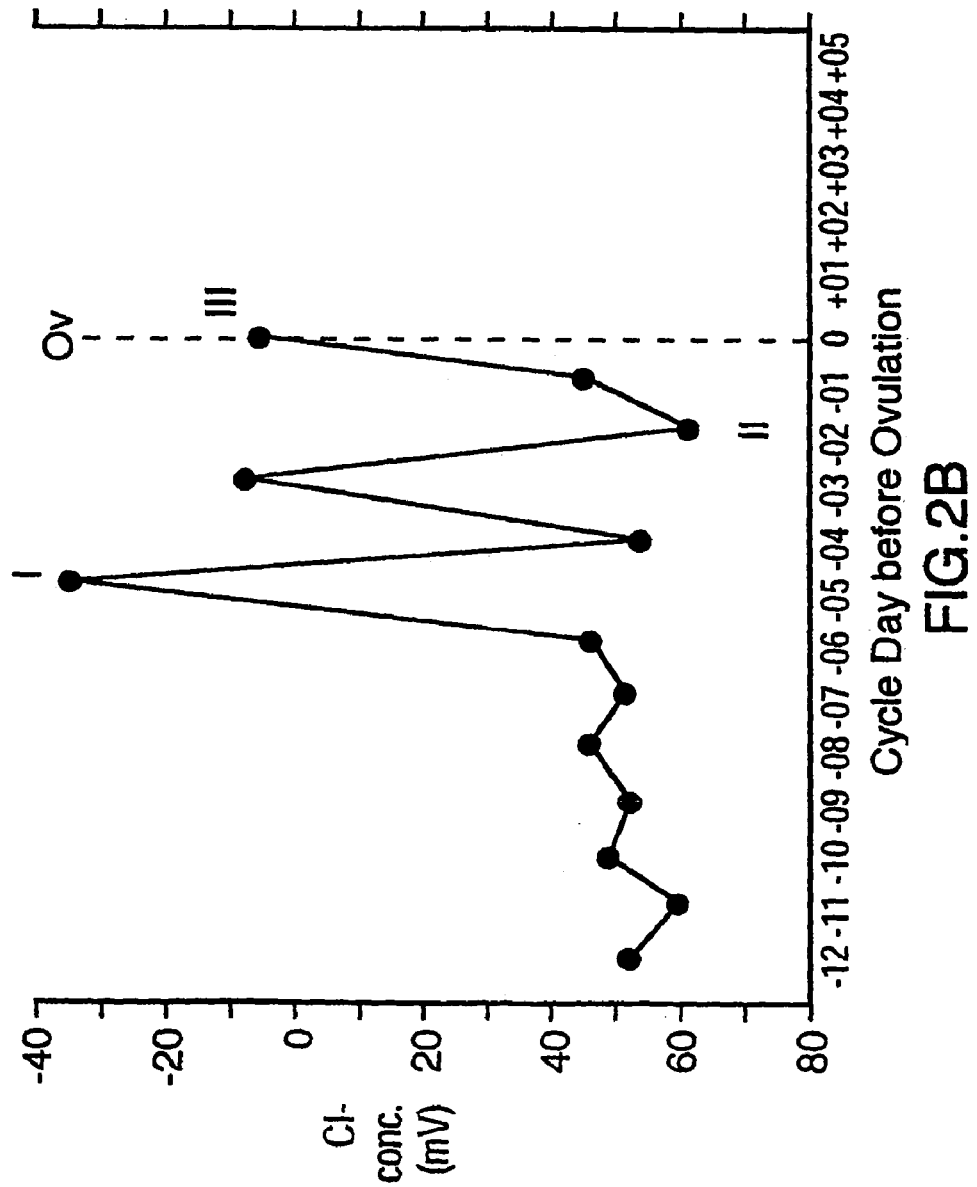
Figure 2C:
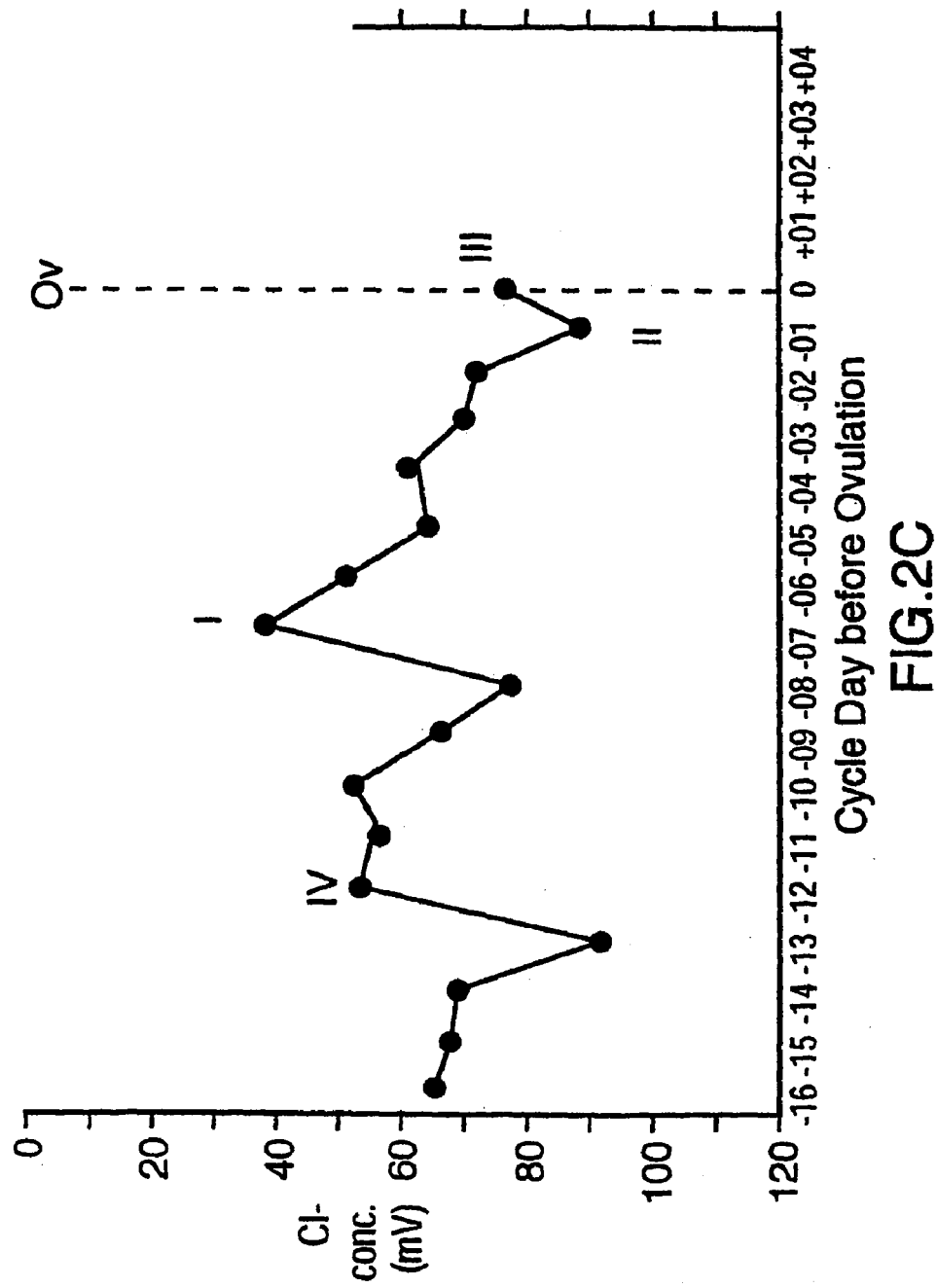

FIGS. 2A to 2C illustrate changes in the concentration of the chloride (Cl−) ions in the eccrine sweat per day for the reproductive cycle of a number of female humans. As illustrated in FIGS. 2A to 2C, there is generally a surge in the chloride (Cl−) concentration of about 25% followed by a decrease of about 40% from the maximum, thereby defining an inversion at point I. This inversion, which for chloride (Cl−) is a maximum, occurs at between three to six days prior to ovulation, similar to the sodium (Na+) ion reading shown in FIGS. 1A to 1D and can be used to predict ovulation, and therefore commencement of the fertile period. Accordingly, monitoring the chloride (Cl−) ion for a distinct change following an inversion can also be used to predict ovulation at about three to six days in advance, and therefore determine the fertile phase of the female human.

The adscissa in FIGS. 2A to 2C is similar to the adscissa in FIGS. 1A to 1D in that it measures the days of the reproductive cycle of a female human. Also, the ovulation is shown to occur on day 0 and is also marked by the vertical dashed line (Ov). However, it is noted that FIGS. 2A and 2B show the Y axis as an inverted millivolt scale. In other words, as the millivolt value decreases or becomes more negative, the graph will increase. This reflects the fact that chloride (Cl−) ions are negative such that when the chloride concentration increases, there is a corresponding decrease, or greater negative value, in the potential of the chloride (Cl−) electrode. Likewise, when there is a decrease in the chloride (Cl−) potential, as occurs following the inversion, there is a corresponding increase, or more positive value, shown at the potential for the chloride (Cl−) electrode. Accordingly, FIGS. 2A and 2B illustrate the change in the chloride (Cl−) ion concentration by providing the outputs in millivolts from the chloride ion, and, for ease of reference, the Y axis has been inverted so that it becomes more negative when it moves upward on the drawing, reflecting an increase in the chloride (Cl−) concentration as the potential becomes more negative. This also assists in comparison with the illustrations in FIGS. 1A to 1C which show the millivolt potential for the sodium (Na+) and potassium (K+) electrodes. In FIGS. 1A to 1C, because the ions are positively charged sodium (Na+) and potassium (K+) ions, an increase in the concentration of these ions will be reflected by a more positive value at the electrode, and therefore an increase in these concentration is illustrated by the graph moving upwards.

Reference is made to FIG. 2A where at point I, there is an inversion which results after a surge in the chloride (Cl−) ion concentration of more than five millivolts, which is more than about 25%. On the sixth day before ovulation, there is a decrease, but not a distinct decrease, such as about 40%. Rather, there is a large decrease from the sixth day to the fifth day of about 40%. Therefore, on day minus five, following the distinct change of about 40%, there will be an indication that the female human is in the fertile phase. In other words, the reading on the sixth day did not indicate a distinct change so as to conclude that an inversion has occurred.

FIG. 2B also illustrates an inversion at day minus five. The inversion is preceded by an increase of at least 25%, or in this case, more than five millivolts, and followed by a distinct change or decrease of at least 40% or in this case, 13 millivolts. It is noted that at day three before ovulation, there is also a similar inversion, but at a much lower concentration. This second inversion at day three before ovulation will be ignored by the present invention at least because an indication would already have been made that the female human is in the fertile phase as of day five before ovulation.

It is noted that FIGS. 2A and 2B also show a portion marked by reference numeral II where the chloride (Cl−) ion concentration reaches a minimum or nadir, as is also shown in FIGS. 1A to 1D. This minimum is believed to coincide with a rise in serum total estrogen 24 to 48 hours prior to ovulation. While one advantage of the present invention is that it would have determined at the inversion I that the female human is in the fertile phase, the portion II could be used to confirm that the female human is in the fertile phase, or even to determine that the female human is now in the fertile status of ovulation. This can be further confirmed by the further increase shown at point III near the day of ovulation "Ov". The portion II is not used to determine the fertile phase in general because the inversion I can determine the fertile phase much earlier.

FIG. 2C is similar to FIGS. 2A and 2B in that it shows the chloride concentration by means of showing the change in the millivolt voltage at the chloride (Cl−) electrode. Likewise, FIG. 2C shows a surge or increase in the chloride (Cl−) concentration between day eight to day seven prior to ovulation which is followed by a distinct change between day seven and day five causing an inversion at point I at day seven before ovulation. FIG. 2C also shows a decrease in chloride (Cl−) concentration one day before ovulation, marked by point II. Finally, FIG. 2C, as with FIGS. 2A and 2B, show a further increase in concentration at the date of ovulation marked by point III.

In addition, FIG. 2C shows an early inversion or peak at day 12 before ovulation, marked by point IV. This point IV is a false inversion point which would not be considered by the system as the inversion which indicates commencement of the fertile phase at least because it occurred too early in the reproductive cycle of the female human. False inversion point IV can be easily discounted by the system estimating the average reproductive cycle of the female human, and subtracting 19 days prior to the expected menstruation and ignoring all data before this time period. The 19 day period arises because the Luteal period is about 14 days from ovulation to menstruation. Accordingly, false peaks, such as that shown at point IV, would be discounted.

FIGS. 3A and 3B illustrate ratiometric measurements with respect to one ion, in the case of FIGS. 3A and 3B, being the sodium (Na+) ion. FIG. 3A shows a ratiometric measurement of ammonium ($NH_4+$) with respect to sodium (Na+), and, indicates an inversion at day two before ovulation. This corresponds with measurements of increases in ammonia ($NH_4+$) which occur at about two to three days before ovulation.

FIG. 3B illustrates a ratiometric measurement of chloride (Cl−) to sodium (Na+). As can be seen from FIG. 3B, this graph is relatively flat, which would be expected because chloride (Cl−) is the counterion for sodium (Na+). Accordingly, a ratiometric measurement of chloride (Cl−) with respect to sodium would not be of great assistance in identifying commencement of the fertile phase in the female human.

FIG. 3C is shown merely for comprehensiveness and shows the ratio of sodium (Na+) to sodium (Na+), which is one, as would be expected.

FIG. 3D shows a ratio of potassium (K+) with respect to sodium (Na+) and, as is the case with FIG. 3B which shows a ratio of chloride (Cl−) with respect to sodium (Na+), does not show any great changes before ovulation. This would also be consistent with sodium and potassium experiencing similar changes in concentration during the reproductive cycle, as illustrated for instance in FIGS. 1A to 1C.

FIG. 3E illustrates a ratiometric measurement of calcium ($Ca_2+$) with respect to sodium ($Na+$). This ratiometric measurement shows a decrease in the relative concentration of the calcium ($Ca_2+$) ion with respect to the sodium ($Na+$) ion about two days before ovulation.

It is apparent from FIGS. 3A to 3E that ratiometric measurements of ions, such as ammonium ($NH_4+$) and calcium ($Ca_2+$) with respect to sodium ($Na+$), can be used to identify an inversion and predict ovulation about two days in advance. By using a ratiometric measurement, fluctuations in total eccrine sweat can be removed, thereby providing a more accurate prediction of ovulation, but generally only about two days in advance of ovulation.

FIGS. 3B and 3D illustrate that ratiometric measurements of chloride ($Cl-$) and potassium ($Ka+$) with respect to sodium are not very useful to predict ovulation. This would be expected as each of chloride ($Cl-$), sodium ($Na+$) and potassium ($K+$) vary about the same during the reproductive cycle, as illustrated in FIGS. 1A to 1D and 2A to 2C.

While not shown in the drawings, corresponding tests with respect to other ions, such as nitrate ($NO_3-$), have shown that nitrate ($NO_3-$) reacts in a similar manner to ammonium ($NH_4+$). Accordingly, FIG. 3A, which illustrates the ratiometric measurements of ammonium ($NH_4+$) with respect to sodium ($Na+$) would be similar to the ratiometric measurements of nitrate ($NO_3-$) with respect to sodium ($Na+$).

By comparing FIG. 3A (for ammonium ($NH_4+$)) and FIG. 3E (for calcium ($Ca_2+$)), it is apparent that the concentrations for these two ions move in opposite directions during the relevant period prior to ovulation. In particular, ammonium ($NH_4+$) with respect to sodium ($Na+$) appears to peak with respect to sodium ($Na+$) two days before ovulation while calcium ($Ca_2+$) appears to have a nadir with respect to sodium two days before ovulation.

Figure 4:
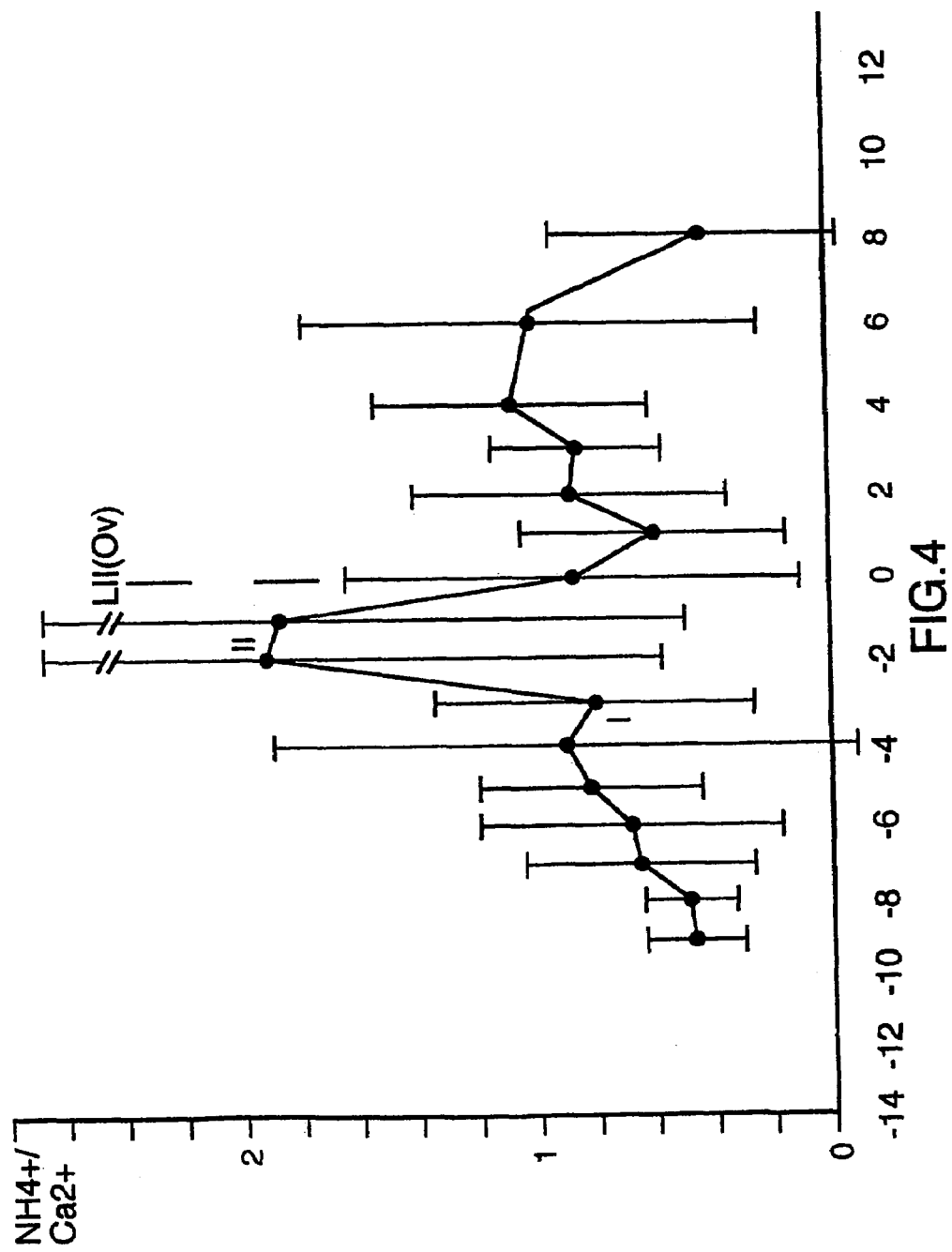
FIG. 4 is a diagram showing ratiometric measurement of ammonium ($NH_4+$) with respect to calcium ($Ca_2+$) during one reproductive cycle of a female human.

Accordingly, rather than taking a ratiometric measurement of one of these ions ($Ca_2+$ or $NH_4+$) with respect to a fairly stable ion, such as sodium ($Na+$) or chloride ($Cl-$), in order to more accurately identify changes in the concentration of the ions in eccrine sweat, the present invention also provides for the ability to take a ratio of two ions which move in opposite directions, such as ammonium ($NH_4+$) and calcium ($Ca_2+$). This is illustrated in FIG. 4 which is a ratiometric measurement of ammonium with respect to calcium ($NH_4+/Ca_2+$). FIG. 4 illustrates an inversion, shown by point I, occurring at about three days before ovulation. This is then followed by a distinct change, in this case an increase in the ratiometric value at two days before ovulation as indicated by point II. Accordingly, a ratiometric measurement between ammonium ($NH_4+$) and calcium ($Ca_2+$) can also be used to identify the fertile phase by predicting ovulation about two to three days in advance. Furthermore, using a ratiometric measurement of ions which move in opposite directions, such as ammonium ($NH_4+$) and calcium ($Ca_2+$), can provide a more pronounced change in the ratiometric value of more than 50% and about 80%, thereby further delineating the inversion I and providing a more accurate measurement to be made.

Figure 5:
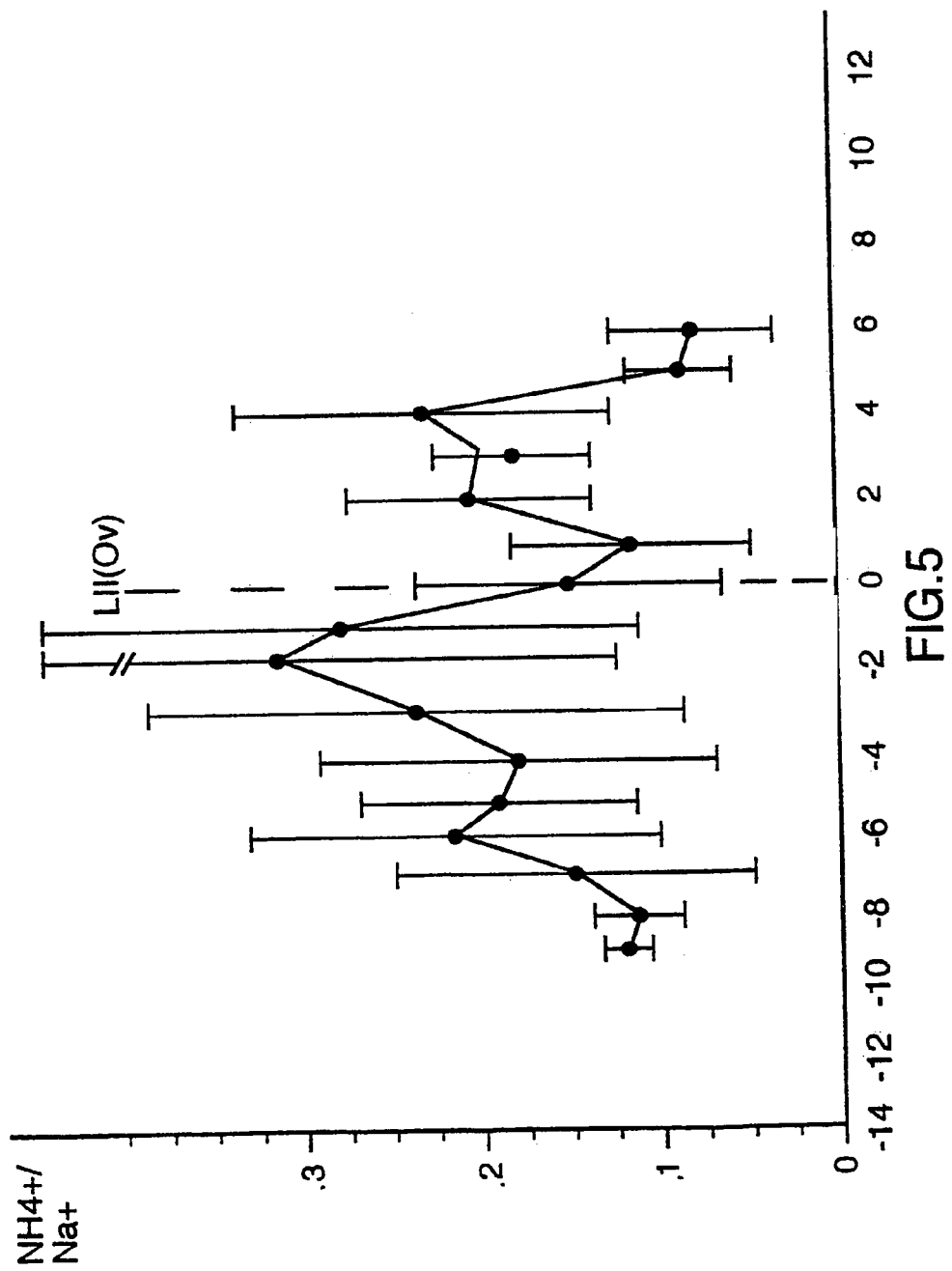
FIG. 5 is a diagram showing ratiometric measurement of ammonium ($NH_4+$) with respect to sodium ($Na+$) during one reproductive cycle of a female human.

FIG. 5 shows a drawing, similar to that shown for FIG. 3A, of a ratiometric value for ammonium ($NH_4+$) with respect to sodium ($Na+$). However, FIG. 5 is more accurate and shows an inversion occurring at about four days before ovulation. Accordingly, FIG. 5 suggests that in some cases, a ratiometric measurement of ammonium ($NH_4+$) with respect to sodium ($Na+$) may show an inversion with a nadir of ammonium ($NH_4+$) with respect to sodium ($Na+$) at day four before ovulation, followed by a distinct rise at day three before ovulation. In such cases, the present invention will indicate that the female human is in the fertile phase at day three before ovulation and provide an earlier measurement than the peak at day two before ovulation. Accordingly, a ratiometric measurement of ammonium ($NH_4+$) with respect to sodium ($Na+$) can predict ovulation at least two days in advance, and in some cases three to four days in advance. FIG. 5 also illustrates that with respect to ratiometric measurements, an inversion, either being a maximum or a minimum, may occur which would be expected because the relative values of ions are being measured and can result in more fluctuation.

Figure 6:
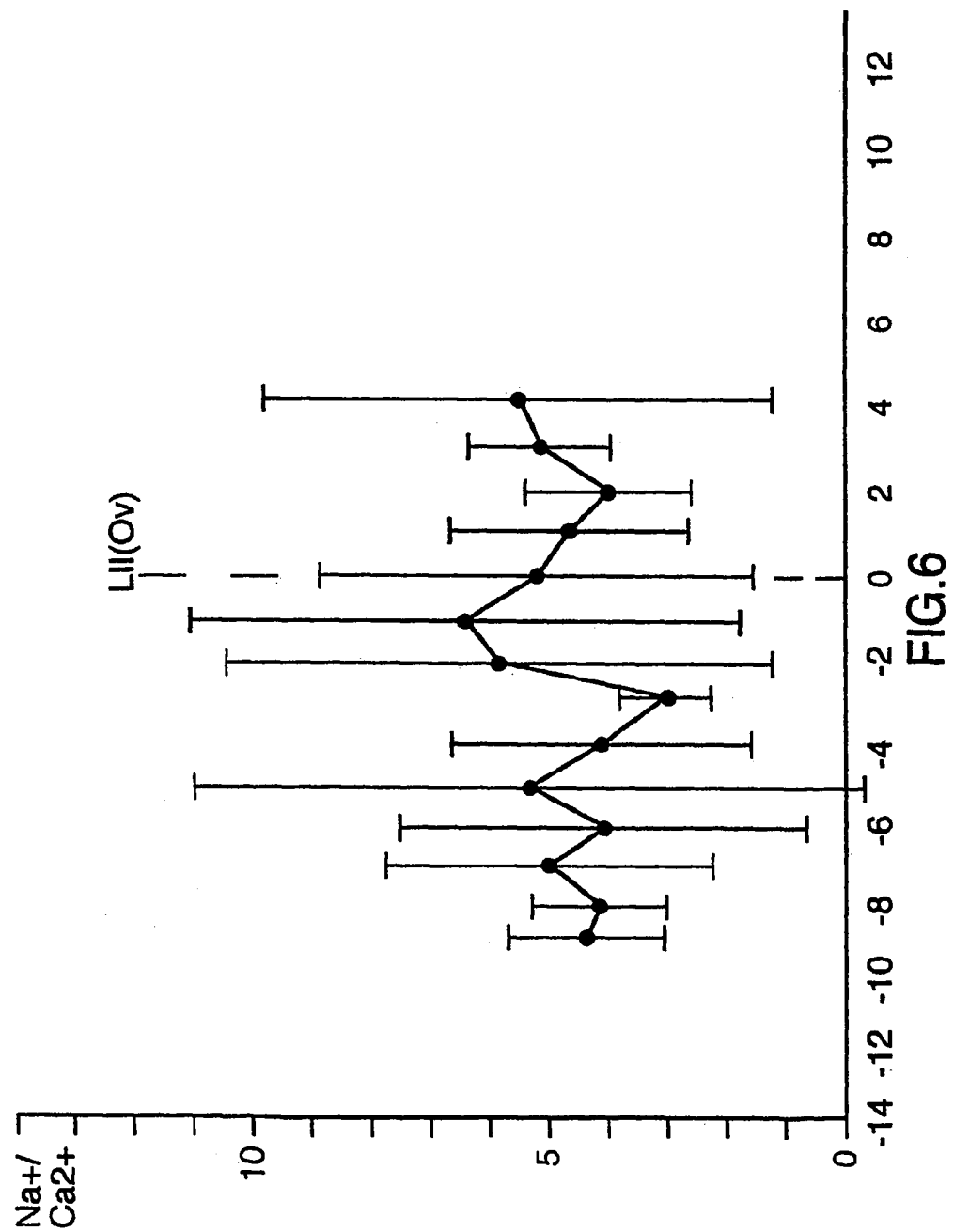
FIG. 6 is a diagram showing ratiometric measurement of sodium ($Na+$) with respect to calcium ($Ca_2+$) during one reproductive cycle of a female human.

FIG. 6 illustrates a ratiometric measurement of sodium ($Na+$) with respect to calcium ($Ca_2+$). FIG. 6 is similar to FIG. 3E, except that FIG. 6 shows the ratio of sodium ($Na+$) with respect to calcium ($Ca_2+$), and therefore is the inversion of the graph shown in FIG. 3E. This is why FIG. 6 shows a peak while FIG. 3E shows a nadir two days before ovulation.

Figure 7:
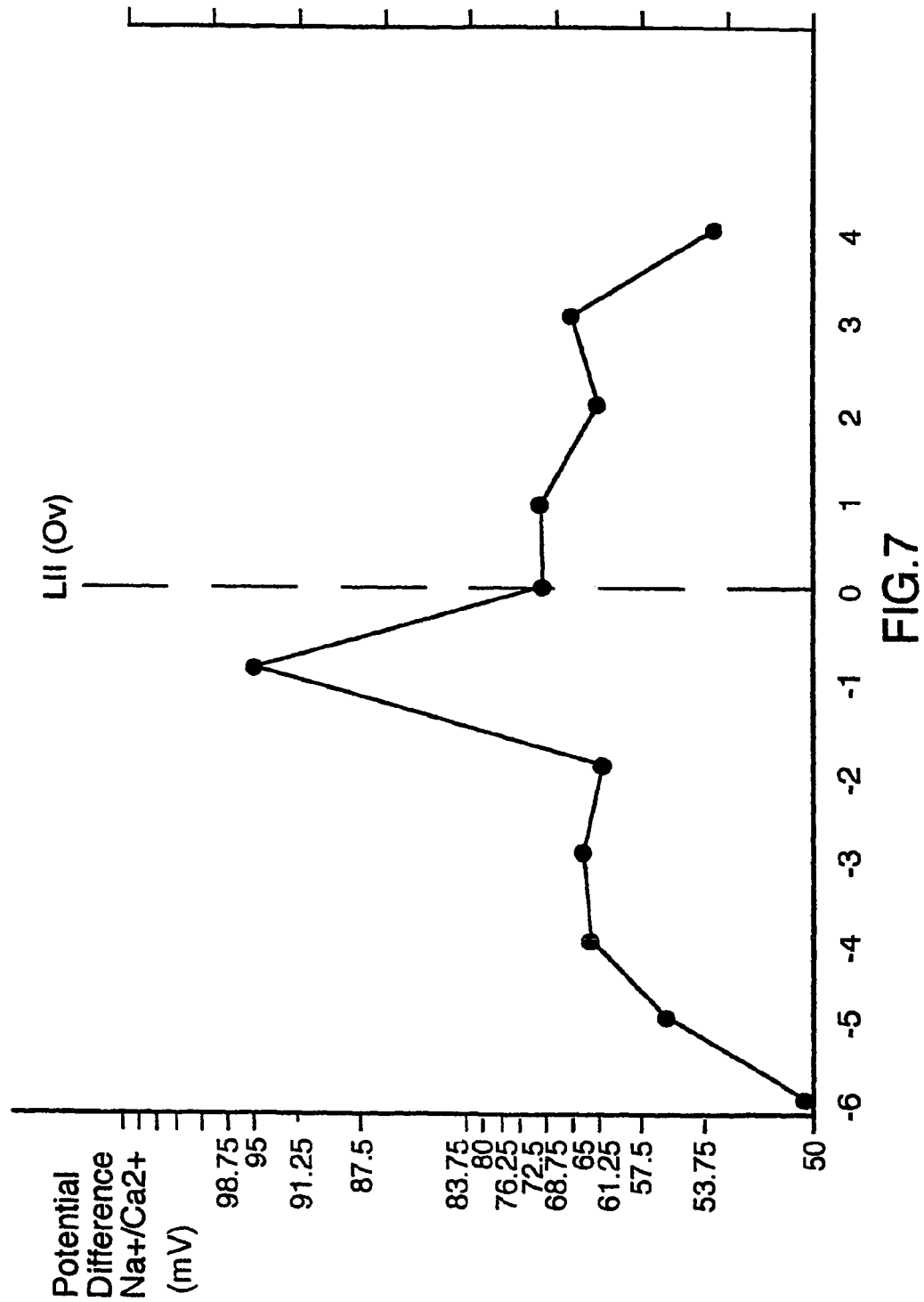
FIG. 7 is a diagram showing a relative ratiometric measurement expressed as potential difference of sodium ($Na+$) with respect to calcium ($Ca_2+$) during one reproductive cycle of a female human.

In another method, rather than determining the concentration of two ions using two ion electrodes and one reference electrode, and then determining the ratio of their concentration, the determination may be simplified by eliminating the reference electrode and simply measuring the potential difference between two sensing electrodes. In this case, the relative ratiometric change in the ion concentrations is detected by the potential difference between the two sensors alone. An example is shown in FIG. 7 for a sodium ($Na+$) electrode with respect to a calcium ($Ca_2+$) electrode, and in FIG. 8 for a chloride ($Cl-$) electrode with respect to a calcium ($Ca_2+$) electrode. To explain by example, in FIG. 7, as the calcium ($Ca_2+$) concentration in the sweat drops with respect to sodium ($Na+$), the calcium ($Ca_2+$) electrode becomes more negative, and thus the potential difference between the two electrodes increases. If the sodium ($Na+$) concentration drops with respect to calcium ($Ca_2+$), electrode potential will decrease.

Figure 8:
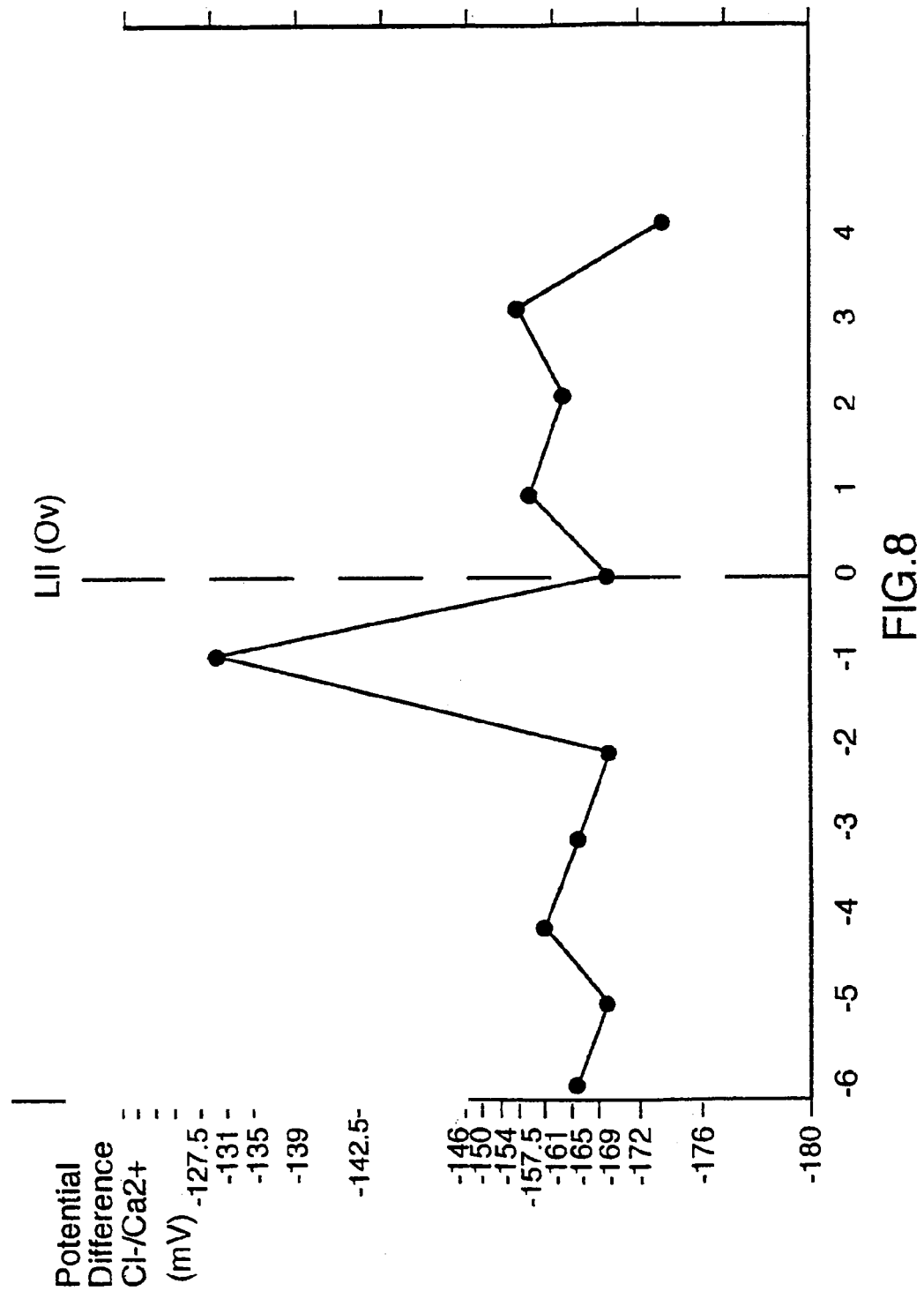
FIG. 8 is a diagram showing a relative ratiometric measurement expressed as potential difference of chloride ($Cl-$) with respect to calcium ($Ca_2+$) during one reproductive cycle of a female human.

As can be seen from FIGS. 7 and 8, a peak can be seen in the curves about one day prior to ovulation in a manner consistent with the ratiometric measurements shown in FIGS. 5 and 6. It should be noted that this method is not as accurate as with the true ratiometric method used in FIGS. 5 and 6, since the changes seen indicate only relative changes in the concentrations of the ions. As well, a divalent ion sensor potential change will only be half that of a monovalent ion for the same concentration change. However, where the ratio changes of the ions in question is large and obvious this method is advantageous in the simplicity it affords to the reduced sensor arrangement, and in particular, to the elimination of the reference electrode.

Figure 9:
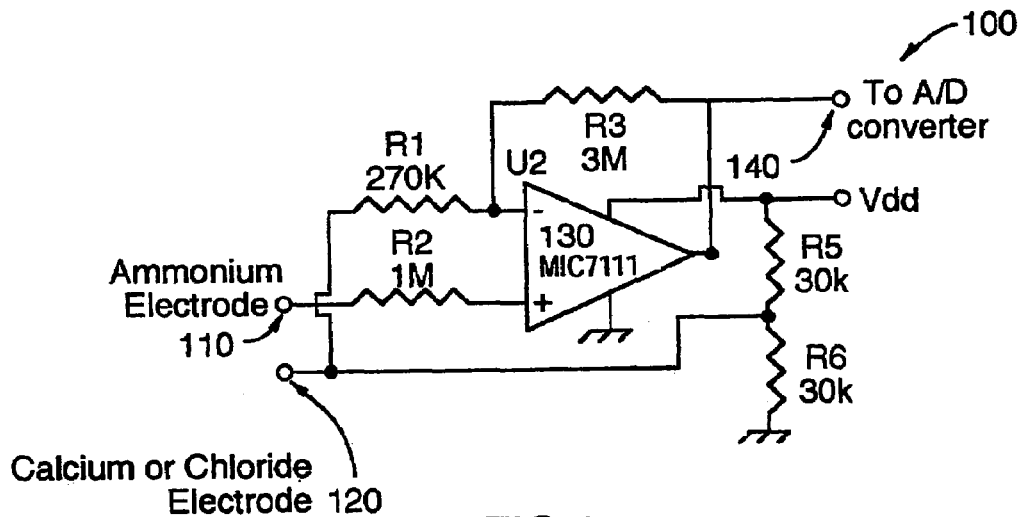
FIG. 9 is a schematic diagram showing a circuit for a device having a sensor for sensing two ions according to one embodiment of the invention.

FIG. 9 illustrates a schematic diagram of a circuit, shown generally by reference numeral 100, to sense one or two ions, according to one preferred embodiment of the present invention. As shown in FIG. 9, the sensor 100 comprises an ammonium ($NH_4+$) electrode 110 and a second electrode, which in FIG. 9 is shown as being either a calcium ($Ca_2+$) or chloride ($Cl-$) electrode 120. Accordingly, the sensor 100 illustrated in FIG. 9 can be used to sense the relative change in concentration of ammonium ($NH_4+$) with respect to either calcium ($Ca_2+$) or chloride ($Cl-$) and provide an output to an analog to digital (A/D) converter at output 140 reflecting a potential difference of these electrodes.

Accordingly, the output 140 for sensor 100 illustrated in FIG. 9 could contain output signals corresponding to a ratiometric measurement of ammonium ($NH_4+$) with respect to calcium ($Ca_2+$) when the second electrode 120 is a calcium ($Ca_2+$) electrode. Therefore, the output signals for such a sensor 100 would be similar to that shown in FIG. 7 or 8 and would be unit independent as it is a ratiometric measurement of relative ion concentration. Likewise, the output 140 for sensor 100 illustrated in FIG. 9 could contain output signals corresponding to a relative ratiometric measurement of ammonium ($NH_4+$) with respect to chloride (Cl−) when the second electrode 120 is a chloride (Cl−) electrode.

As also illustrated in FIG. 9, the sensor 100, in one preferred embodiment, comprises an operational amplifier 130, which in this embodiment is Model MIC7111, and provides about ten times amplification of the relative potential between the first electrode 110 and the second electrode 120. The sensor 100 in this preferred embodiment also comprises resistors R1, R2, R3, R5, R6 and an input voltage Vdd to provide amplification and stability for the sensor 100.

Figure 11:
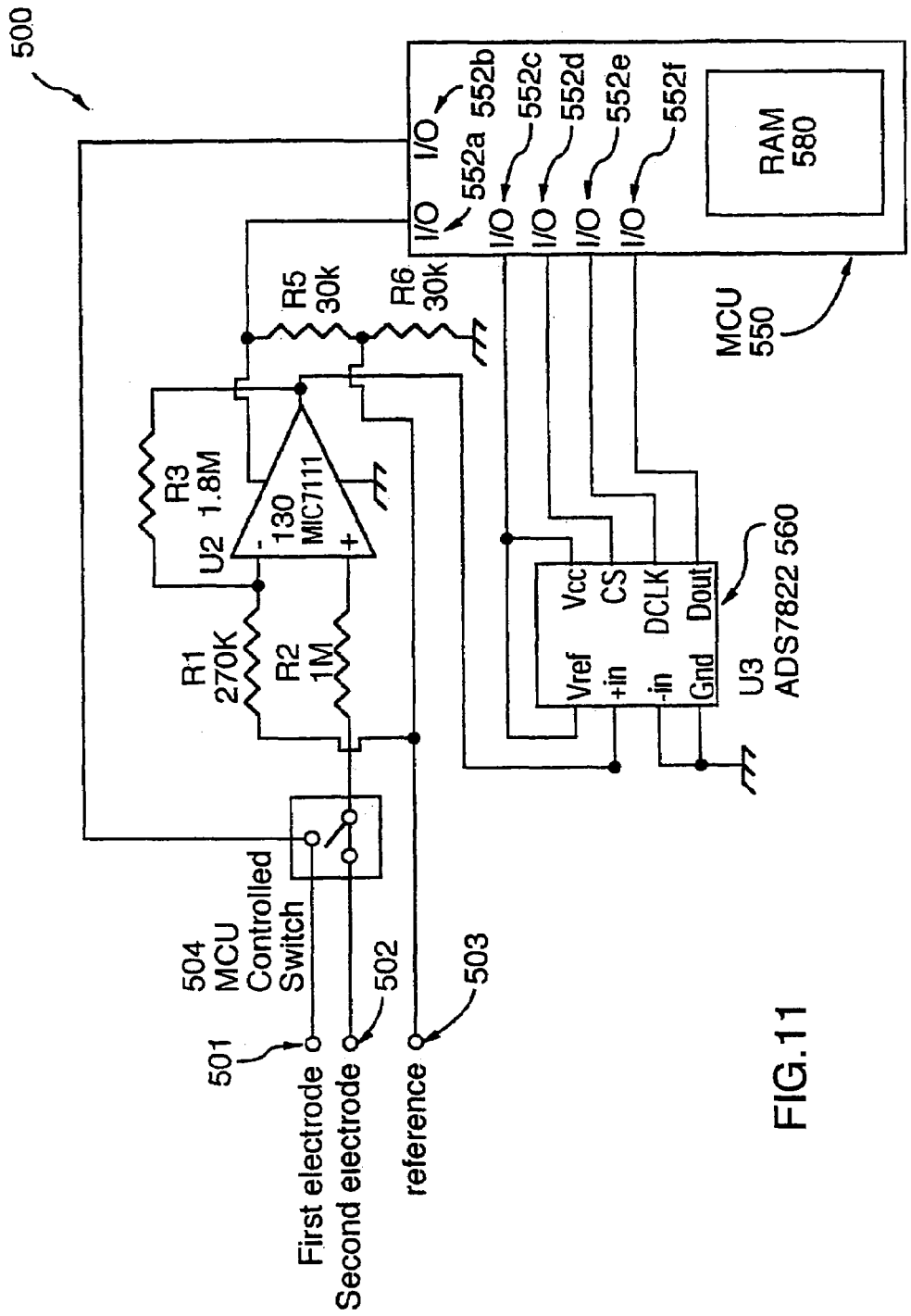
FIG. 11 illustrates a schematic diagram showing a circuit for a device having a sensor for sensing two ions with respect to a reference according to one embodiment of the invention.

The output electrode 140 is shown in FIG. 9 as being connected to an A/D converter circuit (not shown). It is understood that the A/D converter circuit (not shown) could be a separate circuit or could form part of a processor, as shown in FIG. 11 by reference numeral 400.

Figure 10A:
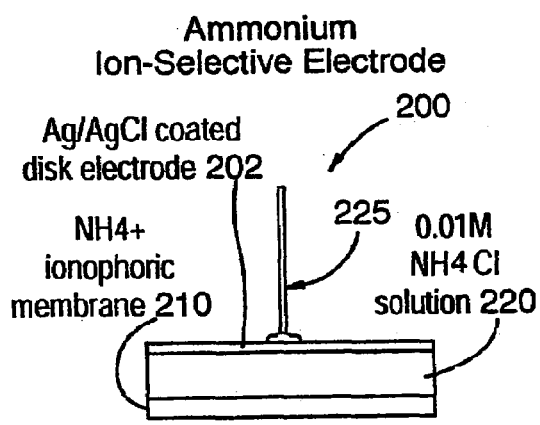
FIGS. 10A, 10B and 10C illustrate electrodes for sensing ammonium ($NH_4+$), chloride ($Cl-$) and calcium ($Ca_2+$), respectively.
Figure 10B:
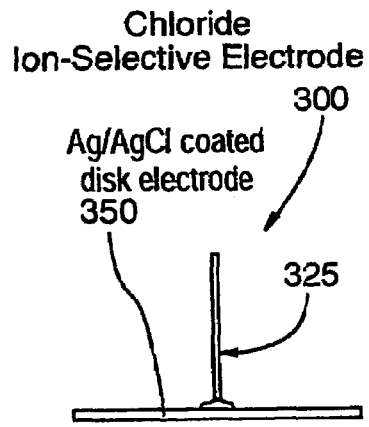
Figure 10C:
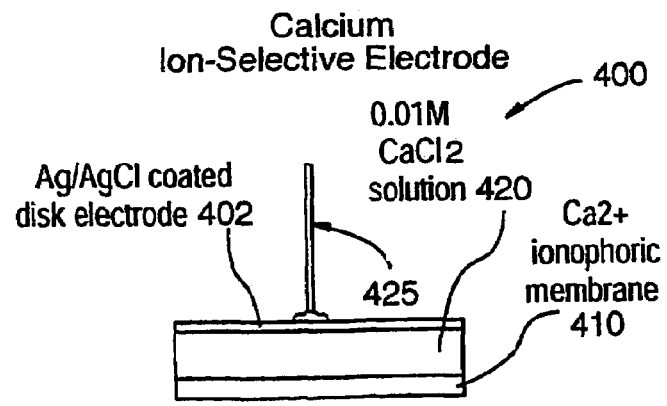

The first electrode 110 and the second electrode 120 could be any known type of electrode for measuring ammonium ($NH_4+$), calcium ($Ca_2+$), chloride (Cl−), or any of the other ions referred to above, such as sodium (Na+), potassium (K+) and nitrate ($NO_3-$). The electrodes 110, 120 could also be a conductivity sensor to sense conductivity (Cond.), as described above with respect to FIGS. 1A to 1C. In this case, the sensor 100 would incorporate an electronic voltage circuit (not shown), as is known in the art, to sense the conductivity (Cond.) between the electrodes. FIGS. 10A to 10C illustrate representations of the electrodes which could be used for the first electrode 110 and the second electrode 120. Electrode 120 could also be a standard reference electrode if the circuit is used to measure the concentration of one ion only with the first electrode 1110 being the appropriate ion sensor. For instance, the measurements of the sodium (Na+), chloride (Cl−) and potassium (K+) ions as illustrated in FIGS. 1A to 1D and 2A to 2C were obtained by having the first electrode 110 being an appropriate electrode to sense sodium (Na+), chloride (Cl−) and potassium (K+), respectively, and the second electrode 120 being a standard reference electrode. In a preferred embodiment, where relative changes in concentration are being measured, the first electrode 110 is selected to sense the concentration of a first ion, such as ammonium ($NH_4+$), and the second electrode 120 is selected to sense a second ion, such as calcium ($Ca_2+$). Other combinations of electrodes 110, 120 to sense concentrations of the different ions described above could be used. This avoids the need for a reference electrode because both electrodes would be measuring the changes in concentrations of a particular ion, and then, a relative ratio could be obtained.

FIG. 10A shows an ammonium ion-selective electrode, shown generally by reference numeral 200, as is known in the art. The ammonium ion-selective electrode 200 comprises a silver/silver chloride-coated disk electrode 202 in electrical contact with a 0.01M solution of ammonium chloride 220 which in turn is in electrical contact with an ammonium ionophoric membrane 210. The ammonium ion-selective electrode 200 will provide an output potential at output 325 which is electrically connected to the disk 202. This output potential will be an electrical output signal with respect to a standard reference electrode which corresponds to the ammonium ($NH_4+$) concentration in the eccrine sweat in contact with the ammonium ionophoric membrane 210.

FIG. 10C shows a calcium ion-selective electrode 400. The calcium ion-selective electrode 400 is similar to the ammonium ion-selective electrode 200 in that it has a silver/silver chloride-coated disk electrode 402, a 0.01M solution of calcium chloride ($CaCl_2$) 420 and a calcium ionophoric membrane 410. The calcium ion-selective electrode 400 can sense the concentration of calcium ($Ca_2+$) ion in the eccrine sweat and produce an output potential at output 325 with respect to a standard reference electrode which is electrically connected to the disk electrode 402. The output potential will be an electrical output signal corresponding to the concentration of the calcium ($Ca_2+$) ion in eccrine sweat.

FIG. 10B shows a chloride ion-selective electrode, shown generally by reference numeral 300. Unlike the ammonium and calcium ion-selective electrodes 200, 400, the chloride ion-selective electrode 300 has a sole silver/silver chloride-coated disk electrode 350. The disk electrode 350 will produce an output potential with respect to a standard reference electrode which can be sent to the output 325. The output potential will be an electrical output signal which corresponds to the concentration of chloride (Cl−) ions in the eccrine sweat.

The electrodes 200, 300 and 400 shown in FIGS. 10A, 10B and 10C can also be used individually in order to sense changes in concentration of a single ion, such as ammonium ($NH_4+$), chloride (Cl−) or calcium ($Ca_2+$) with respect to a standard reference electrode. For instance, the silver/silver chloride-coated disk electrode 350 could be used to sense the chloride (Cl−) ion concentration which can be used to determine the fertile phase as described above with respect to FIGS. 2A to 2C. Similarly, known electrodes and sensors to sense other characteristics of eccrine sweat, such as sodium (Na+), nitrate ($NO_3-$) and potassium (K+) ion concentrations and conductivity could also be used. In addition, the electrodes 200, 300 and 400, as well as similar known electrodes and sensors to sense other characteristics of eccrine sweat, such as sodium (Na+), nitrate ($NO_3-$) and potassium (K+), could be used connected to the first electrode 110 or second electrode 120 to provide changes in relative concentrations of two ions. As discussed above, because the present invention monitors changes in concentrations, rather than absolute concentrations, measurements provided, such as by the relative potential of two electrodes, is sufficient to operate the invention.

FIG. 11 shows a schematic diagram of a sensor, shown generally by reference numeral 500, according to a further embodiment of the present invention.

The sensor 500 is similar to the sensor 100 in that it comprises an amplifier 130, which is model MIC7111 and resistors R1, R2, R3, R5 and R6 to complete the circuit. However, FIG. 11 differs in that it has three electrodes, namely a first sensor electrode 501, a second sensor electrode 502 and a reference electrode 503. The sensor electrodes 501 and 502 can be any type of electrode to sense the concentration of an ion in the eccrine sweat, such as calcium ($Ca_2+$), chloride (Cl−), ammonium ($NH_4+$), shown in FIGS. 10A to 10C, or any other ions to sense another ion or conductivity. Likewise, reference 503 can be a standard reference electrode, or alternatively, can provide a potential indicative of the concentration of a reference ion, such as chloride (Cl−), sodium (Na+) or potassium (K+) in the eccrine sweat to provide ratiometric measurements, as illustrated above in FIGS. 3A to 3E, 4, 5 and 6.

Sensor 500 also comprises a switch 504 which is controlled by the microcomputer 550 to switch between taking measurements of the sensor electrode 501 or the sensor electrode 502. In other words, the microprocessor 550 can take two separate ratiometric measurements, namely a first ratiometric measurement of the potential of the sensor 501 with respect to the reference 503, and a second ratiometric measurement of the potential of the sensor 501 with respect to the potential of the reference 503. The microprocessor 550 can then compare these two separate ratiometric measurements to provide a further, more accurate ratiometric measurement.

In a preferred embodiment, the sensor 501 is an ammonium ($NH_4+$) electrode, such as electrode 200 shown in FIG. 10A, the sensor 502 is a calcium ($Ca_2+$) electrode, such as the electrode 400 shown in FIG. 10C and the reference electrode 503 is a chloride (Cl−) electrode 300 as shown in FIG. 10B. In this way, ratiometric measurements of ammonium ($NH_4+$) with respect to a reference ion, such as chloride (Cl−), and then calcium ($Ca_2+$) with respect to the same reference ion, can be obtained and transferred to the microprocessor 550. The microprocessor 550 will then compare the ratiometric measurements of ammonium ($NH_4+$) with respect to chloride (Cl−) and also the ratiometric measurement of calcium ($Ca_2+$) with respect to chloride (Cl−) to provide a ratiometric measurement of ammonium ($NH_4+$) with respect to calcium ($Ca_2+$). However, because this final ratiometric measurement of ammonium ($NH_4+$) with respect to calcium ($Ca_2+$) was initially with respect to a reference ion, such as chloride (Cl−), the effects with respect to the volume of eccrine sweat, as well as accumulation of ions on the skin can be removed. Accordingly, sensor 500 can be used to provide a more accurate measurement of the relative concentration of ammonium ($NH_4+$) with respect to calcium ($Ca_2+$). In addition to chloride (Cl−), sodium (Na+) and potassium (K+) could also be used as reference ions.

As shown in FIG. 11, the sensor 500 shows the switch 504 being controlled by one of the output ports 552b. The second output port 552a provides power to the sensor circuit as required. The integrated circuit 560 receives the relative potential signal from the amplifier 130, and in this preferred embodiment, comprises an analog to digital converter, to convert the analog signal from the amplifier 130 to a digital signal which can be processed by the microprocessor 550. Input/output ports 552c, 552d, 552e and 552f are connected to a clock and integrated circuit 560 to assist in running a sensor 500, as is known in the art.

The microprocessor unit 550 also generally contains memory so as to store the various measurements made during the day. In this way, a daily average based on a number of readings can be obtained. Furthermore, the microprocessor 550 to count out periods of time, such as 30 or 60 minute intervals, so that readings can be taken throughout the day and averaged. Preferably, the readings are taken at the same time each day so that any changes in the concentration of ions in eccrine sweat due to daily variations, either to diet or activity, will not adversely affect the results.

In a preferred embodiment, the microprocessor unit 550 causes the sensor 100, 500 to sense the concentration of at least one of the ions at least six times per day. In this way, the processor can accumulate at least six readings per day, and preferably more, and use these six readings in a statistical analysis to provide a daily average of the concentration. The statistical analysis may include eliminating one or more of the readings which are considered spurious and/or fitting the readings to a gaussian distribution in order to more clearly determine the average. In more sophisticated embodiments, readings taken at the same time during the day will be given more weight in order to account for and eliminate differences which may arise in the concentration of the ions during a day.

The daily averages can be stored in any type of known storage device contained within the device 500. In a more advanced system, the readings can be transmitted to a remote location, such as by wireless transmission and/or non-wireless transmission, and then stored and analyzed at the remote location, such as a central computing or monitoring laboratory.

The processor 550 also preferably contains some random access memory (RAM), shown generally by reference numeral 580, which can store various information, and in particular readings and or results of previous reproductive cycles. Accordingly, the daily readings can be stored in the RAM 580 and/or downloaded, either through a serial connection or a wireless connection, for further analysis and/or record keeping by a remotely located computer or the processor 550. The results of previous reproductive cycles can also be used to estimate the duration of the reproductive cycle for each female, as described above. This provides an estimate of the commencement of the reproductive cycle, and thereby permits the processor 550 to discount or ignore earlier spurious readings, as described above for instance with respect to FIG. 2C.

Figure 12:
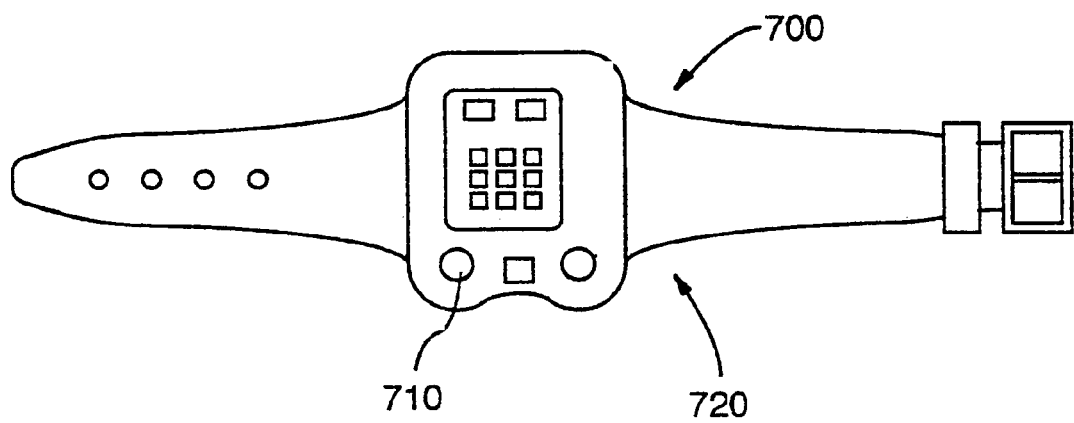
FIG. 12 is an exploded view of an apparatus which can be strapped to the wrist and used with a microprocessor to effect measurement of the concentration of ions in the eccrine sweat according to one embodiment of the present invention.

FIG. 12 is a diagram showing the device 700 according to one embodiment of the present invention. As shown in FIG. 12, the device comprises a display 710 for displaying, amongst other things, the fertility status of the female. Initially, the display 710 will indicate that the female is not fertile. Once the determination is made that the female is in the fertile phase, the display 710 indicates that the female is fertile, followed by an indication again that the female is again not fertile after one day following ovulation. Optionally, the display 710 may also display "Ov" indicating that the device 700 has determined that the female is ovulating.

As also shown in FIG. 12, the device 700 comprises a strap 720 such that the device 700 can be strapped to the surface of the skin of the user for extended periods of time. This facilitates taking readings over a longer period of time, such as several hours during the day and/or night, without adversely impacting on the mobility of the user. Furthermore, in a preferred embodiment, the device 700 comprises a clock which displays the time over the period of the day so that the device 700 can appear as a regular wrist watch. Also, because the device 700 is attached to the surface of the skin of the user for extended periods of time and comprises a clock, the device 700 can automatically and repeatedly take readings in 30 or 60 minute intervals, or other time intervals, as described above, throughout the day without the user even being aware that the readings are being taken.

In a further preferred embodiment, the device 700 is manufactured from a plastic material and has on the side opposite the display 710 a flat plastic surface which promotes sweating when placed against the skin of the user. In a further preferred embodiment, the device 700 comprises a flange around an area in order to pool the eccrine sweat at a location near the location of the sensors 100, 500. This facilitates sweating and pooling of the eccrine sweat near the sensors 100, 500 so that more accurate readings can be obtained.

It is understood that both ionophoric and solid state sensors, as well as other types of sensors, could be used to determine the concentration of ions in eccrine sweat. In a preferred embodiment, solid state sensors, in particular when chloride (Cl−) ions are being sensed, have been found to be very stable.

It is understood that the present invention has been defined with respect to use by a woman, which has also been referred to as a female human. However, the present invention is not limited to use by female humans. Rather, the present invention has applicability with other mammals which excrete eccrine sweat and can be used in the veterinarian field. Moreover, the present invention has been found to be useful with respect to pigs, horses and bovine. However, it is understood that some of the time periods and indicators may change for other mammals.

It will be understood that, although various features of the invention have been described with respect to one or another of the embodiments of the invention, the various features and embodiments of the invention may be combined or used in conjunction with other features and embodiments of the invention as described and illustrated herein.

Although this disclosure has described and illustrated certain preferred embodiments of the invention, it is to be understood that the invention is not restricted to these particular embodiments. Rather, the invention includes all embodiments which are functional, electrical or mechanical equivalents of the specific embodiments and features that have been described and illustrated herein.

The invention claimed is:

1. A device for determining a fertile phase of a female human comprising:
   (a) a sensor for sensing concentrations of at least two ions in the eccrine sweat of the female, said at least two ions comprising at least a first ion and a second ion different from the first ion, said sensor comprising a first electrode for sensing the concentration of the first ion and a second electrode for sensing the concentration of the second ion, and generating output signals indicative of concentrations of the at least two ions in the eccrine sweat;
   (b) a processor for controlling the sensor to sense the concentrations of at least two ions in the eccrine sweat substantially simultaneously and at least on a daily basis; and
   wherein the processor monitors the output signals from the sensor to identify a distinct change in the concentration of one of the at least two ions following an inversion during a single menstrual cycle of the female which indicative of the female human being in the fertile phase.

2. A device as claimed in claim 1, wherein the at least two ions sensed in the eccrine sweat are selected from the group consisting of sodium (Na+), potassium (K+), ammonium ($NH_4+$), calcium ($Ca_2+$), chloride (Cl−) and nitrate ($NO_3-$) of the eccrine sweat.

3. A device as claimed in claim 2, wherein to identify a distinct change in the concentration of one of the least two ions following an inversion, the processor monitors the output signals to identify a surge of 25% followed by a drop of 40% in the concentration of at least one of the first ion and the second ion.

4. The device as claimed in claim 1, wherein the processor monitors a ratio of the concentration of the first ion to the second ion to identify a distinct change in the concentration of the at least two ions following an inversion indicating the female human is in the fertile phase.

5. The device as claimed in claim 4, wherein the first ion is selected from the group consisting of potassium (K+), nitrate ($NO_3-$), ammonium ($NH_4+$) and calcium ($Ca_2+$), and, a second ion is selected from the group consisting of sodium (Na+) and chloride (Cl−).

6. The device as claimed in claim 4, wherein the first ion is ammonium ($NH_4+$) and the second ion is calcium ($Ca_2+$).

7. A device as claimed in claim 4, wherein the device further comprises a display for displaying characters indicating the female human is in the fertile phase.

8. A device as claimed in claim 4, further comprising a fastener for fastening the device to the female subject such that the sensor contacts the skin of the female at least six hours each day; and
   wherein the processor controls the sensor to sense the concentration of the at least two ions between eight to eighteen times each day to monitor a daily average of the concentrations.

9. A device as claimed in claim 4, wherein the fertile state of ovulation is predicted to occur within six days following the inversion.

10. The device as claimed in claim 4, wherein the first ion is selected from the group consisting of potassium (K+), nitrate ($NO_3-$) and ammonium ($NH_4+$), and the second ion is selected from the group consisting of calcium ($Ca_2+$).

11. The device as claimed in claim 10, wherein the at least two ions comprise a third ion selected from the group consisted of sodium (Na+) and chloride (Cl−); and
   wherein the processor monitors a first preliminary ratio of the concentration of the first ion with respect to the third ion, and, a second preliminary ratio of the concentration of the second ion with respect to the third ion, and, the processor then monitors a ratio of the first preliminary ratio to the second preliminary ratio to identify a distinct change in the concentration of the at least two ions following an inversion indicating commencement of a fertile phase.

12. A device for determining the fertility status of a female mammal comprising:
   (a) a sensing means for sensing at least one ion selected from the group consisting of potassium (K+), ammonium ($NH_4+$), calcium ($Ca_2+$), chloride (Cl−), nitrate ($NO_3$) and sodium (Na+), in the eccrine sweat of the female mammal and generating output signals indicative of the concentration of ions in the eccrine sweat;
   (b) processor means for controlling the sensing means to sense the at least one ion in the eccrine sweat at least on a daily basis; and
   wherein the processor means monitors the output signals stored in the storage means to identify a distinct change in a concentration of one of the at least one ions following an inversion during a single menstrual cycle of the mammal which is indicative of the female mammal is in the fertile phase,
   wherein the female mammal is a female human and the distinct change is a change of at least 40% following the inversion.

13. A device as claimed in claim 12, wherein the device further comprises a display means for indicating the female mammal is in the fertile phase.

14. A device as claimed in claim 12, wherein the sensing means utilizes a solid state sensor.

15. The device defined in claim 12, wherein the processor causes the sensing means to sense the concentration of the at least one ion at least six readings per day and statistically analyzes the at least six readings to provide an average of the concentration for the day; and
   wherein the processor means monitors the average of the concentration of one of the at least one ions to identify a distinct change in the concentration of one of the at least one ions following an inversion which indicates the female human is in the fertile phase.

16. A device as claimed in claim 12, wherein the female mammal is a female human and ovulation is ascertained to occur within six days following the inversion.

17. The device as defined in claim 12, further comprising:
   storage means for storing information regarding previous reproductive cycles of the female; and
   wherein the processor utilizes the information to predict an expected duration of the reproductive cycle and disregard output signals obtained for an initial portion of a reproductive cycle of the female mammal immediately following menstruation.

18. The device as defined in claim 17, wherein the initial portion which is disregarded is prior to 19 days before an estimated end of the reproductive cycle.

19. The device as claimed in claim 18, wherein the at least one ion comprises a first ion and a second ion different from the first ion, and the processor monitors a ratio of the concentration of the first ion to the second ion to identify a distinct change in the concentration of the one of the at least one ion following an inversion during a single menstrual cycle of the female mammal which indicates the female mammal is in the fertile phase.

20. The device as claimed in claim 19, wherein the first ion is selected from the group consisting of potassium (K+), nitrate ($NO_3-$), ammonium ($NH_4+$) and calcium ($Ca_2+$), and, a second ion is selected from the group consisting of sodium (Na+) and chloride (Cl−).

21. A method for determining a fertile phase of a female human comprising the steps of:
   (a) sensing concentration of at least two ions, comprising a first ion and a second ion different from the first ion, in eccrine sweat of the female human substantially simultaneously and at least on a daily basis by sensing the concentration of the first ion using a first electrode sensitive to the first ion and by sensing the concentration of the second ion using a second electrode sensitive to the second ion;
   (b) generating output signals indicative of concentrations of the at least two ions in the eccrine sweat; and
   (c) monitoring the output signals to identify a distinct change in the concentration of one of the at least two ions following an inversion during a single menstrual cycle of the female human which indicates the female human is in the fertile phase.

22. The method as defined in claim 21, wherein step (c) further comprises the step of:
   (i) monitoring the output signals to identify a surge of at least 25% followed by a drop of at least 40% in the concentration of at least one of the first ion and the second ion indicating the female human is in the fertile phase.

23. The method as defined in claim 21, wherein the at least two ions sensed in the eccrine sweat are selected from the group consisting of sodium (Na+), potassium (K+), ammonium ($NH_4+$), calcium ($Ca_2+$), chloride(Cl−) and nitrate ($NO_3-$) of the eccrine sweat.

24. The method as defined in claim 21 comprising the further steps of:
   sensing concentrations of the least two ions substantially simultaneously and at least six times a day;
   generating output signals indicative of concentrations of the at least two ions in the eccrine sweat;
   processing the output signals to provide a daily average of the at least two ions; and
   monitoring the daily averages of the output signals to identify a distinct change in the concentration of one of the at least two ions following an inversion during a single menstrual cycle which indicates the female human is in the fertile phase.

25. The method as defined in claim 21 further comprising the steps of:
   storing information regarding previous reproductive cycles of the female; and
   predicting, based on the stored information regarding previous reproductive cycles of the female, an expected duration of the reproductive cycle and disregarding output signals prior to 19 days before an estimated end of the expected duration of the reproductive cycle.

26. The method as defined in claim 21, wherein step (c) comprises the step of:
   (i) monitoring a ratio of the concentration of the first ion to the second ion to identify a distinct change in the concentration of one of the at least two ions following an inversion during a single menstrual cycle which is indicative the female human being is in the fertile phase.

27. The method as defined in claim 26, wherein the first ion is selected from the group consisting of potassium (K+), nitrate ($NO_3-$), ammonium ($NH_4+$) and calcium ($Ca_2+$), and, a second ion is selected from the group consisting of sodium (Na+) and chloride (Cl−).

28. The method as defined in claim 26, wherein the first ion is selected from the group consisting of nitrate ($NO_3-$) and ammonium ($NH_4+$) and the second ion is selected from the group consisting of calcium ($Ca_2+$).

* * * * *